US011368640B2

(12) United States Patent
Ofuji et al.

(10) Patent No.: US 11,368,640 B2
(45) Date of Patent: Jun. 21, 2022

(54) IMAGING APPARATUS AND IMAGING SYSTEM

(71) Applicant: CANON KABUSHIKI KAISHA, Tokyo (JP)

(72) Inventors: Masato Ofuji, Takasaki (JP); Jun Kawanabe, Saitama (JP); Kentaro Fujiyoshi, Tokyo (JP); Sho Sato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 377 days.

(21) Appl. No.: 16/709,808

(22) Filed: Dec. 10, 2019

(65) Prior Publication Data

US 2020/0213543 A1 Jul. 2, 2020

(30) Foreign Application Priority Data

Dec. 26, 2018 (JP) ............................. JP2018-243140

(51) Int. Cl.
*G01T 1/20* (2006.01)
*H04N 5/359* (2011.01)
*G01T 1/208* (2006.01)
*A61B 6/00* (2006.01)
*H04N 5/378* (2011.01)
*H01L 27/146* (2006.01)

(52) U.S. Cl.
CPC ........... *H04N 5/359* (2013.01); *A61B 6/4233* (2013.01); *A61B 6/4258* (2013.01); *G01T 1/208* (2013.01); *G01T 1/20183* (2020.05); *H01L 27/14636* (2013.01); *H01L 27/14676* (2013.01); *H04N 5/378* (2013.01)

(58) Field of Classification Search
CPC .......... H04N 5/359; H04N 5/378; H04N 5/32; A61B 6/4233; A61B 6/4258; A61B 6/44; A61B 6/54; A61B 6/542; G01T 1/20183; G01T 1/208; H01L 27/14636; H01L 27/14676; G01N 23/04
See application file for complete search history.

(56) References Cited

U.S. PATENT DOCUMENTS 10,904,459 B2 * 1/2021 Matsumiya ............ H04N 5/378
2013/0306873 A1 * 11/2013 Jun ....................... G01T 1/2018
250/361 R

FOREIGN PATENT DOCUMENTS

JP 2013-235934 A 11/2013
JP 2014-75377 A 4/2014

* cited by examiner

*Primary Examiner* — Kiho Kim
(74) *Attorney, Agent, or Firm* — Canon U.S.A., Inc. IP Division

(57) ABSTRACT

An imaging apparatus includes a pixel region including a plurality of pixels, and bias wiring laid on a light incident side of pixels to supply a bias from a power supply to the pixels in the pixel region via a second side defining the pixel region. The bias wiring includes first wiring portions and second wiring portions laid around the pixels. The first wiring portions are laid in a Y direction away from the second side, and the second wiring portions are laid in an X direction orthogonal to the Y direction. The first wiring portions include a light non-transmissive member. A resistance of the first wiring portion per pixel is smaller than that of the second wiring portion per pixel. A loss of light due to the second wiring portion is smaller than that of the light incident due to the first wiring portion.

10 Claims, 16 Drawing Sheets

FIG.8

| | OPENING RATIO | CALCULATION CONDITION | | CALCULATIONS (CROSSTALK) | |
|---|---|---|---|---|---|
| | | Rv (Ω) | Rh (Ω) | AVERAGE | DISTRIBUTION (DIFFERENCE BETWEEN MAXIMUM AND MINIMUM VALUES) |
| FIRST EXEMPLARY EMBODIMENT | 88% | 1 | 5 | -0.16% | 0.01% |
| FIRST COMPARATIVE EXAMPLE | 93% | 5 | 5 | -0.40% | 0.01% |
| SECOND COMPARATIVE EXAMPLE | 84% | 1 | 1 | -0.16% | 0.01% |
| SECOND EXEMPLARY EMBODIMENT | 90% | 1 | 300 | -0.15% | 0.07% |

FIG.10

| no. | CALCULATION CONDITION | | CALCULATIONS (CROSSTALK) | |
|---|---|---|---|---|
| | Rv (Ω) | Rh (Ω) | AVERAGE | DISTRIBUTION (DIFFERENCE BETWEEN MAXIMUM AND MINIMUM VALUES) |
| #1 | 0.25 | 4 | -0.13% | 0.01% |
| #2 | 1 | 4 | -0.16% | 0.01% |
| #3 | 4 | 4 | -0.34% | 0.01% |
| #4 | 4 | 16 | -0.34% | 0.01% |
| #5 | 4 | 40 | -0.34% | 0.03% |
| #6 | 4 | 400 | -0.32% | 0.09% |
| #7 | 4 | 4000 | -0.32% | 0.11% |
| #8 | 4 | $4 \times 10^6$ | -0.32% | 0.12% |
| #9 | 4 | $4 \times 10^9$ | -0.32% | 0.12% |

IMAGING APPARATUS AND IMAGING SYSTEM

BACKGROUND OF THE INVENTION

Field of the Invention

The present disclosure relates to an imaging apparatus and an imaging system. In particular, the present disclosure is suitably applicable to a radiation imaging apparatus and a radiation imaging system that capture a radiographic image of an object.

Description of the Related Art

Imaging apparatuses for medical image diagnosis and nondestructive inspection using radiations such as X-rays use a sensor substrate that is a glass or other support substrate on which pixels for detecting radiations are arranged in a two-dimensional matrix. For example, an indirect conversion sensor substrate includes pixels including photoelectric conversion elements made of amorphous silicon (a-Si) on a glass or other support substrate and switch elements composed of thin-film transistors (TFTs), and various types of wiring. Such a sensor substrate is used in combination with a scintillator (phosphor) that converts incident radiation into light. Examples of the wiring include control wiring for controlling the switch elements, signal wiring for taking electrical signals out of the photoelectric conversion elements, and bias wiring for supplying a bias voltage for the photoelectric conversion elements to perform photoelectric conversion with to an interior of the pixel region. For example, FIG. 1 of Japanese Patent Application Laid-Open No. 2014-75377 illustrates a sensor substrate on which bias wiring is vertically and laterally laid around the pixels in a mesh shape.

To minimize wiring resistance, the bias wiring is typically made of a light non-transmissive metal layer, not a light transmissive transparent conductive layer. In such a case, part of the light occurring from the scintillator is blocked by the bias wiring and the rest of the light is incident on the photoelectric conversion elements.

If a radiation with a high intensity is incident on part of the sensor substrate, i.e., the amount of radiation becomes nonuniform within an effective pixel region of the sensor substrate, crosstalk can occur. Of these, crosstalk occurring in parallel with control lines laid in a lateral direction (lateral crosstalk) is troublesome during high speed driving of a moving image sensor in particular. Since the lateral crosstalk occurs from instantaneous local variations in the bias voltage supplied from a power supply, one effective measure is to lower the resistance of the bias wiring within the sensor substrate to reduce the foregoing variations in the bias voltage.

In the sensor substrate discussed in Japanese Patent Application Laid-Open No. 2014-75377, the line width of the bias wiring can be increased to lower the resistance of the bias wiring. This, however, increases the area of overlap between the bias wiring and the pixels as seen in the incident direction of light, with a drop in an opening ratio.

In other words, conventional techniques have difficulty in achieving low crosstalk while maintaining a high opening ratio.

SUMMARY OF THE INVENTION

The present disclosure is directed to an imaging apparatus that achieves low crosstalk while maintaining a high opening ratio.

According to an aspect of the present disclosure, a pixel region including a plurality of pixels arranged in a two-dimensional matrix, the pixels each including a photoelectric conversion element and a switch element electrically connected to one of electrodes of the photoelectric conversion element, and bias wiring laid on a light incident side of the photoelectric conversion element to supply a bias from a power supply to each pixel in the pixel region from a side defining the pixel region, the bias wiring being laid around the pixel in a first direction away from the side and a second direction orthogonal to the first direction, the bias wiring being electrically connected to the other electrode of the photoelectric conversion element, wherein the bias wiring includes a first wiring portion laid in the first direction and a second wiring portion laid in the second direction, and wherein an opening ratio of the pixels based on the first and second wiring portions is 85% or more, and an absolute value of average crosstalk over the second direction is 0.39% or less.

According to another aspect of the present disclosure, an imaging apparatus includes a pixel region including a plurality of pixels arranged in a two-dimensional matrix, the pixels each including a photoelectric conversion element and a switch element electrically connected to one of electrodes of the photoelectric conversion element, and bias wiring laid on a light incident side of the photoelectric conversion element to supply a bias from a power supply to each pixel in the pixel region from a side defining the pixel region, the bias wiring being laid around the pixel in a first direction away from the side and a second direction orthogonal to the first direction, the bias wiring being electrically connected to the other electrode of the photoelectric conversion element, wherein the bias wiring includes a first wiring portion laid in the first direction and a second wiring portion laid in the second direction, and wherein a resistance of the first wiring portion per pixel is smaller than a resistance of the second wiring portion per pixel, and a loss of light incident on the photoelectric conversion element due to the second wiring portion is smaller than a loss of the light incident on the photoelectric conversion element due to the first wiring portion.

According to the present disclosure, low crosstalk can be achieved while maintaining a high opening ratio.

Further features of the present disclosure will become apparent from the following description of exemplary embodiments with reference to the attached drawings.

BRIEF DESCRIPTION OF THE DRAWINGS

FIG. 8 is a chart illustrating examples of an opening ratio, resistances, and crosstalk calculations in exemplary embodiments of the present disclosure and comparative examples.

FIG. 10 is a chart illustrating examples of crosstalk calculations for various combinations of the resistances illustrated as a calculation condition in FIG. 8.

FIG. 16 is a diagram illustrating an example of a schematic configuration of a radiation imaging system where the radiation imaging apparatus according to any one of the exemplary embodiments of the present disclosure is built in.

DESCRIPTION OF THE EMBODIMENTS

Modes (exemplary embodiments) for carrying the present disclosure will be described below with reference to the drawings. In each of the following exemplary embodiments of the present disclosure, an example where a radiation imaging apparatus that performs imaging using radiations is applied as an imaging apparatus according to the present disclosure will be described. In the following exemplary embodiments of the present disclosure, radiations may include α-rays, β-rays, and γ-rays that are beams of particles (including photons) emitted by radioactive decay, as well as beams having equivalent or higher energy, such as X-rays, particle beams, and cosmic rays.

A first exemplary embodiment of the present disclosure will initially be described.

Figure 1:
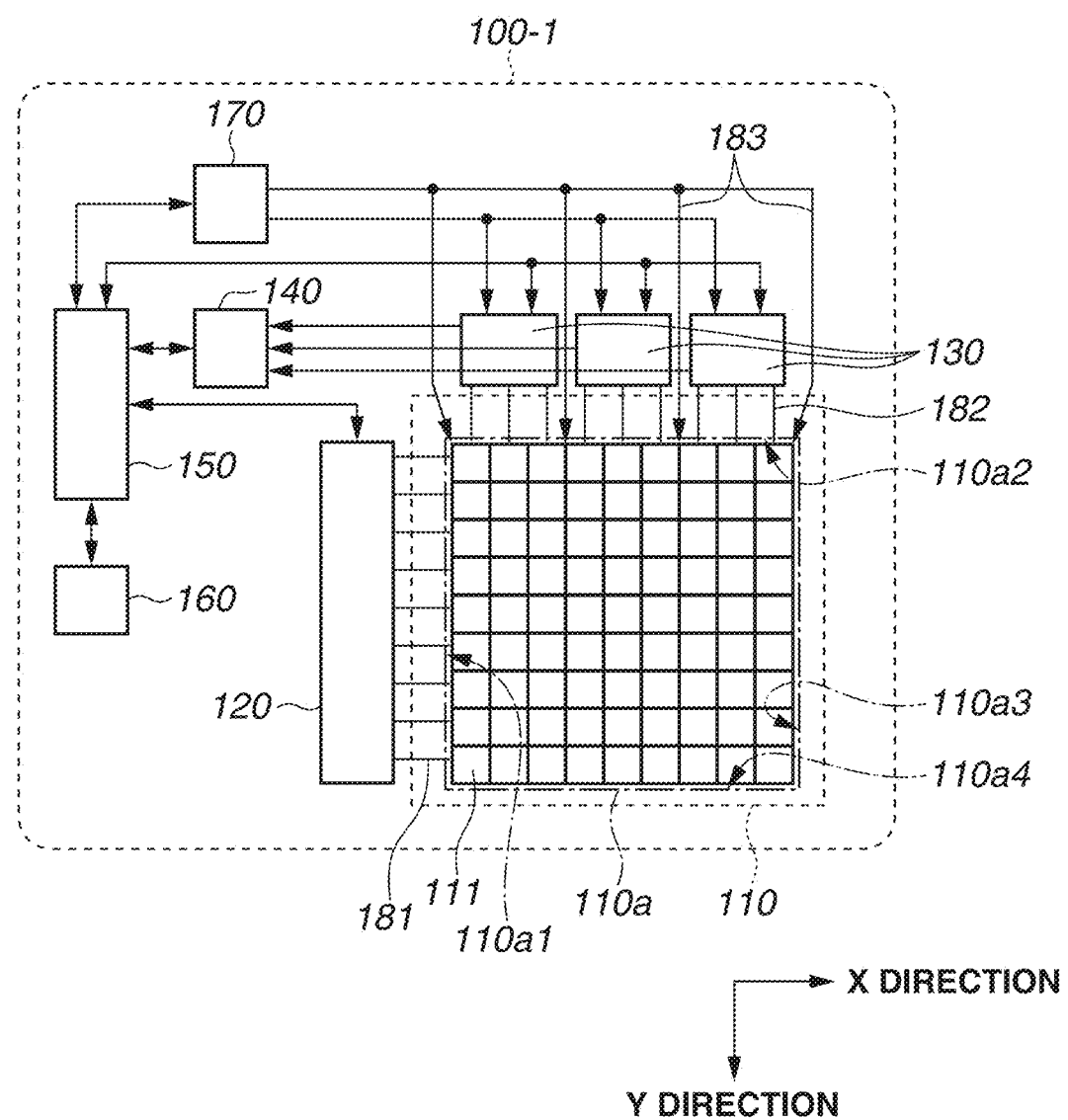
FIG. 1 is a diagram illustrating an example of a schematic configuration of a radiation imaging apparatus according to a first exemplary embodiment of the present disclosure.

FIG. 1 is a diagram illustrating an example of a schematic configuration of a radiation imaging apparatus 100 according to the first exemplary embodiment of the present disclosure. In the following description, the radiation imaging apparatus 100 illustrated in FIG. 1 will be referred to as a "radiation imaging apparatus 100-1".

As illustrated in FIG. 1, the radiation imaging apparatus 100-1 includes a sensor substrate 110, a driving circuit 120, reading circuits 130, a signal processing unit 140, a control unit 150, a communication unit 160, and a power supply circuit 170.

The sensor substrate 110 includes an effective pixel region 110a where a plurality of pixels 111 that detects radiations and generates electrical signals based on the detected amounts of radiation is arranged in a two-dimensional array.

The effective pixel region 110a typically includes a plurality of pixels 111 in a two-dimensional array as large in scale as around 3000×3000 pixels. For want of space, FIG. 1 schematically illustrates 9×9 pixels. In the example illustrated in FIG. 1, the effective pixel region 110a is defined by four sides including a first side 110a1, a second side 110a2, a third side 110a3, and a fourth side 110a4. In the example illustrated in FIG. 1, the driving circuit 120, the reading circuits 130, and the power supply circuit 170 are each connected to one of the four sides 110a1 to 110a4 defining the effective pixel region 110a.

The driving circuit 120 is connected to the pixels 111 in the effective pixel region 110a from the first side 110a1 of the effective pixel region 110a via control wiring 181, and drives the respective pixels 111. Specifically, the driving circuit 120 controls driving of the pixels 111 in the effective pixel region 110a via the control wiring 181 to output electrical signals.

The reading circuits 130 are connected to the pixels 111 in the effective pixel region 110a from the second side 110a2 of the effective pixel region 110a via signal wiring 182. The reading circuits 130 read the electrical signals from the respective pixels 111 and output values based on the electrical signals.

The driving circuit 120 and the reading circuits 130 may be silicon (Si) integrated circuit (IC) chips. Such chips are electrically connected to the sensor substrate 110 by chip-on-film/anisotropic-conductive-film (COF/ACF) packaging or chip-on-glass (COG) packaging. The driving circuit 120 and the reading circuits 130 may be divided into a plurality of chips. In the example illustrated in FIG. 1, the reading circuits 130 are three separate chips. However, the present exemplary embodiment is not limited to such a configuration. The reading circuits 130 may be configured as a single chip or divided into other than three chips. In the example illustrated in FIG. 1, the driving circuit 120 is a single chip. However, the present exemplary embodiment is not limited to such a configuration, and the driving circuit 120 may be configured as a plurality of chips.

The signal processing unit 140 generates a radiographic image by using the values obtained from the reading circuits 130.

The control unit 150 controls operation of the entire radiation imaging apparatus 100-1 in a centralized manner and performs various types of processing.

The communication unit 160 communicates with not-illustrated other external apparatuses such as a control computer.

The power supply circuit 170 supplies power to the driving circuit 120, the reading circuits 130, the signal processing unit 140, the control unit 150, and the communication unit 160, and supplies a bias voltage to the pixels 111 in the effective pixel region 110a through bias supply lines 183. In the example illustrated in FIG. 1, there are a total of four bias supply lines 183, two between the three chips of the reading circuits 130 and two at both sides. The bias supply lines 183 connect the power supply circuit 170 to the second side 110a2 of the effective pixel region 110a. In other words, the power supply circuit 170 supplies the bias voltage to the respective pixels 111 in the effective pixel region 110a from the second side 110a2 of the effective pixel region 110a via the bias supply lines 183.

Figure 2A:
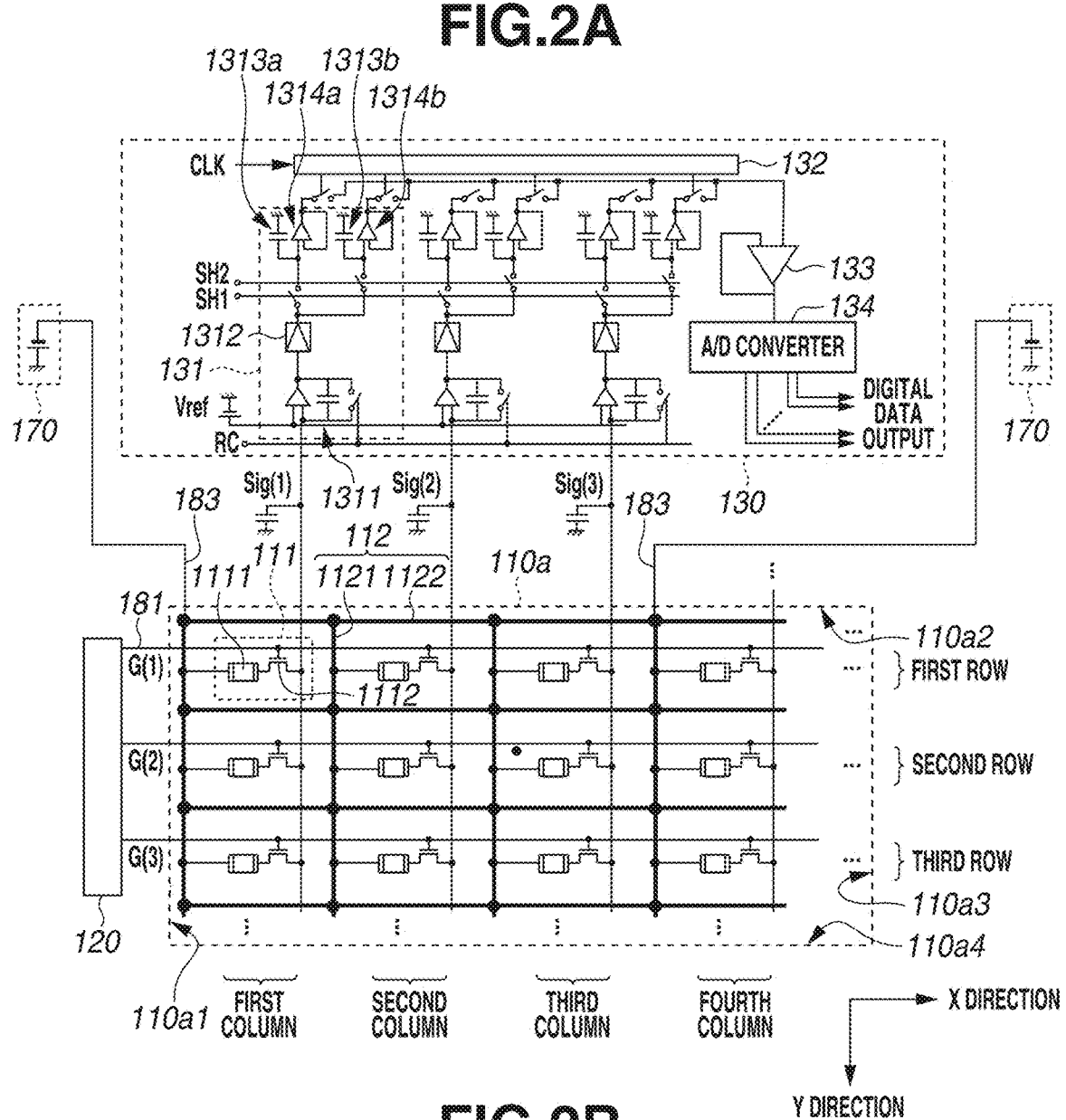
FIGS. 2A and 2B are diagrams illustrating an example of an internal configuration of an effective pixel region and a reading circuit illustrated in FIG. 1.
Figure 2B:
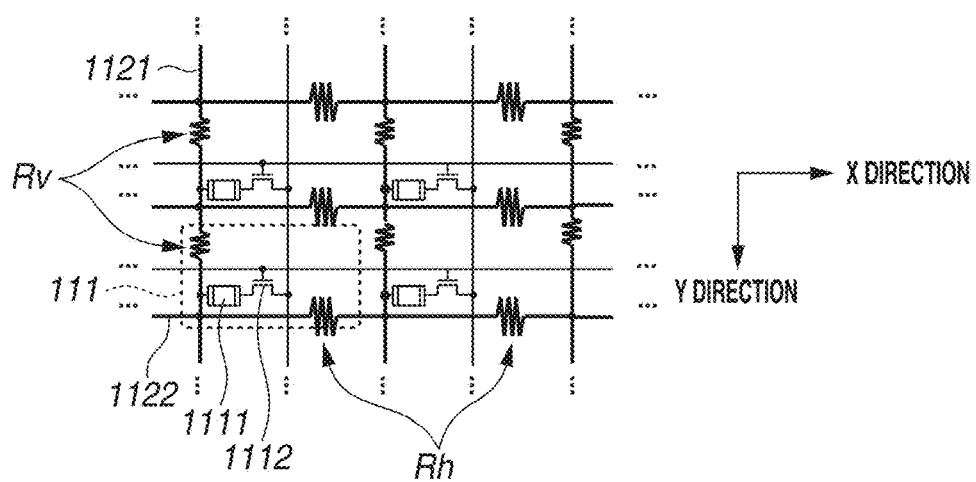

FIGS. 2A and 2B are diagrams illustrating an example of an internal configuration of the effective pixel region 110a and the reading circuits 130 illustrated in FIG. 1. In FIGS. 2A and 2B, components similar to those illustrated in FIG.

1 are designated by the same reference numerals. A detailed description thereof will be omitted.

Specifically, FIG. 2A illustrates an example of the internal configuration of the effective pixel region 110a and a reading circuit 130 illustrated in FIG. 1. More specifically, FIG. 2A illustrates 4×3 pixels 111 at the top left of the effective pixel region 110a among the pixels 111 in the effective pixel region 110a illustrated in FIG. 1, and only one reading circuit 130.

As illustrated in FIG. 2A, each pixel 111 includes a photoelectric conversion element 1111 and a switch element 1112. The photoelectric conversion element 1111 converts incident light occurring from a not-illustrated scintillator layer (specifically, scintillator layer 541 illustrated in FIGS. 5A and 5B) into a charge serving as an electrical signal. The switch element 1112 outputs an electrical signal based on the charge.

In the present exemplary embodiment, the photoelectric conversion element 1111 is a p-intrinsic-n (PIN) photodiode. A metal-insulator-semiconductor (MIS) diode may be used instead. In the present exemplary embodiment, the switch element 1112 is a thin-film transistor (TFT) including a control electrode (gate electrode) and two main electrodes (source and drain electrodes). In the present exemplary embodiment, the channel layer of the TFT is made of amorphous silicon (a-Si). Other materials may be used instead. One of the electrodes of the photoelectric conversion element 1111 is electrically connected to either one of the two main electrodes of the switch element 1112. The other electrode of the photoelectric conversion element 1111 is electrically connected to the power supply circuit 170 via bias wiring 112 and the bias supply lines 183.

All the pixels 111 included in the sensor substrate 110 are commonly connected to the bias wiring 112. The bias voltage is supplied from the power supply circuit 170 to the photoelectric conversion element 1111 of each pixel 111 through the bias wiring 112. The bias wiring 112 is laid inside the effective pixel region 110a to extend between the pixels 111 (around the pixels 111) vertically (in a Y direction, column direction, or first direction) and laterally (in an X direction, row direction, or second direction) in a mesh shape. Specifically, the bias wiring 112 is laid around the pixels 111 in a vertical direction (Y direction, column direction, or first direction) away from the second side 110a2 of the effective pixel region 110a where the power supply circuit 170 is electrically connected, and in a lateral direction (X direction, row direction, or second direction) orthogonal to the vertical direction. In the following description, the wiring portions of the bias wiring 112 laid in the vertical direction (Y direction, column direction, or first direction) will be referred to as "first wiring portions 1121". The wiring portions laid in the lateral direction (X direction, row direction, or second direction) will be referred to as "second wiring portions 1122". The bias wiring 112 is located on the light incident side of the photoelectric conversion elements 1111. The bias wiring 112 and other lines actually have electrical resistances. Of these, the resistance of the bias wiring 112 will be described below with reference to FIG. 2B.

FIG. 2B is an equivalent circuit diagram of 2×2 pixels 111 extracted from the effective pixel region 110a, with an emphasis on the resistance of the bias wiring 112 illustrated in FIG. 2A. FIG. 2B illustrates the first wiring portions 1121 and the second wiring portions 1122 described above. In the present exemplary embodiment, the resistance of the bias wiring 112 will be referred to as follows: A resistance of the first wiring portion 1121 per pixel 111 is Rv. A resistance of the second wiring portion 1122 per pixel 111 is Rh. In the following description, Rv=1Ω and Rh=5Ω. However, the present exemplary embodiment is not limited to such a configuration. For example, the present exemplary embodiment is also applicable to a configuration where the resistance Rv of the first wiring portion 1121 per pixel 111 is smaller than the resistance Rh of the second wiring portion 1122 per pixel 111.

The sensor substrate 110 is electrically connected to the driving circuit 120 via control lines G(1), G(2), G(3), . . . (hereinafter, referred to collectively as control wiring 181). The control terminals of the switch elements 1112 in a plurality of pixels 111 constituting each row are commonly connected to the control wiring 181. The driving circuit 120 makes the pixels 111 output electrical signals by supplying a driving signal for controlling the conducting state of the switch elements 1112 to the respective pixels 111 of the sensor substrate 110 row by row through the control wiring 181 based on a control signal supplied from the control unit 150.

The sensor substrate 110 is electrically connected to the reading circuits 130 via signal lines Sig(1), Sig(2), Sig(3), . . . (hereinafter, referred to collectively as signal wiring 182). The other main electrodes (main electrodes to which the photoelectric conversion elements 1111 are not connected) of the switch elements 1112 in a plurality of pixels 111 constituting each column are commonly connected to the signal wiring 182. Electrical signals based on the charges accumulated in the photoelectric conversion elements 1111 while the switch elements 1112 are in the conducting state are output to the signal wiring 182. The electrical signals are read by the reading circuits 130.

Each reading circuit 130 includes a plurality of amplification circuits 131, a multiplexer 132, a buffer amplifier 133, and an analog-to-digital (A/D) converter 134. The amplification circuits 131 each include an integrating amplifier 1311, a variable amplifier 1312, sample-and-hold circuits 1313 (1313a and 1313b), and buffer amplifiers 1314 (1314a and 1314b). A reset switch of the integrating amplifier 1311 is turned on based on a control signal RC supplied from the control unit 150, whereby the integrating amplifier 1311 is reset. The variable amplifier 1312 amplifies an electrical signal supplied from the integrating amplifier 1311 and outputs the amplified electrical signal. The sample-and-hold circuits 1313 each include a sampling switch and a sampling capacitor. The sample-and-hold circuits 1313 sample and hold the electrical signal supplied from the variable amplifier 1312 based on control signals SH1 and SH2 supplied from the control unit 150. The electrical signals held by the sample-and-hold circuits 1313 are output from the amplification circuit 131 through the buffer amplifiers 1314.

Figure 3:
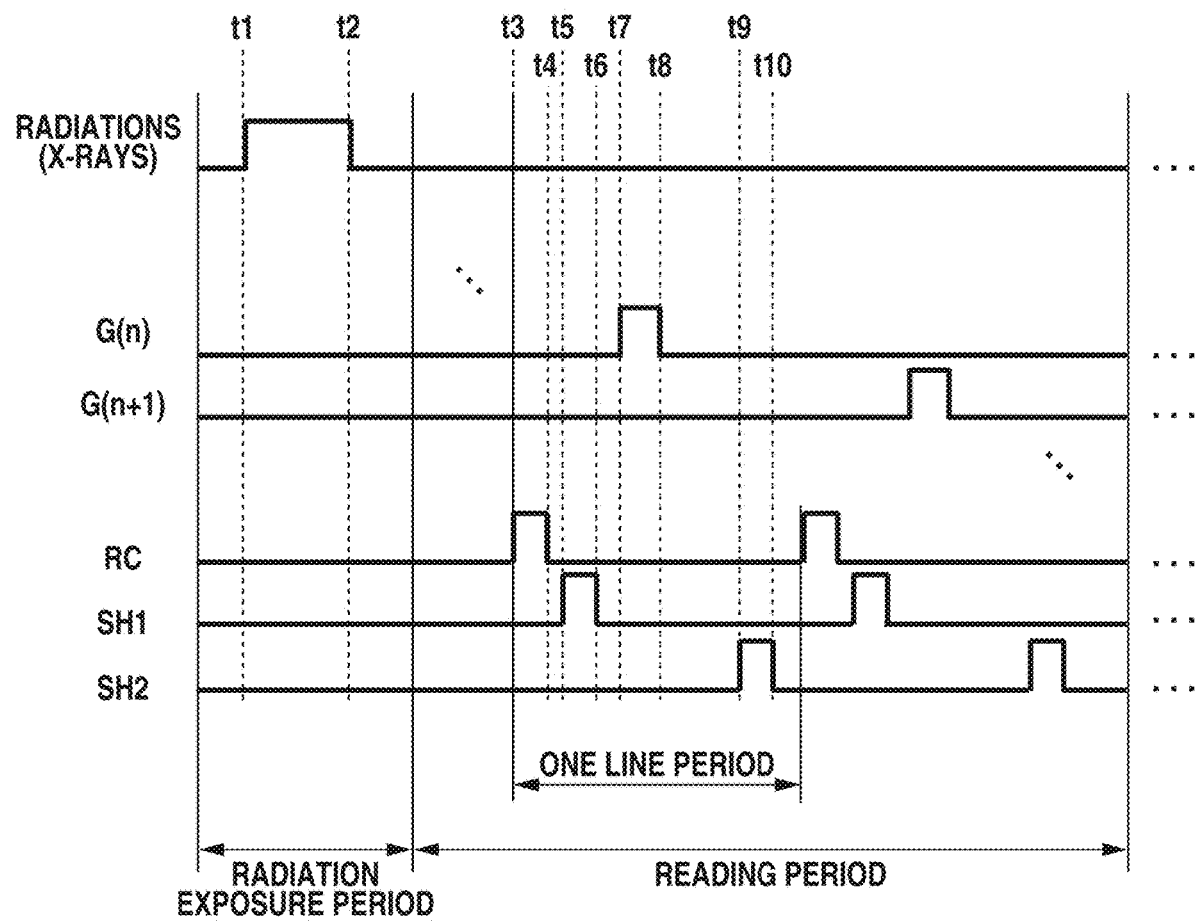
FIG. 3 is a timing chart illustrating an example of a method for operating the internal configuration of the effective pixel region and the reading circuit illustrated in FIGS. 2A and 2B.

FIG. 3 is a timing chart illustrating an example of a method for operating the internal configuration of the effective pixel region 110a and the reading circuit 130 illustrated in FIGS. 2A and 2B. For the control wiring 181, FIG. 3 illustrates only an nth-row control line G(n) and an (n+1)th-row control line G(n+1).

The radiation imaging apparatus 100-1 alternates between a radiation exposure period and a reading period in the following manner. Initially, in times t1 to t2 of the radiation exposure period, the effective pixel region 110a is exposed to radiations. The radiation imaging apparatus 100-1 then enters the reading period. In times t3 to t4, the control signal RC becomes a high level, and the reset switches enter the conducting state. The potential of the signal wiring 182 is thereby reset to a reference potential Vref. In times t5 to t6, the control signal SH1 becomes a high level. The variable amplifiers 1312 output signals based on the amounts of charge accumulated on the signal wiring 182. The output signals here are sampled by the sample-and-hold circuits 1313$a$. In times t7 to t8, the potential of the control signal G(n) becomes a high level. The switch elements 1112 in the nth row enter the conducting state. Charges flow from the photoelectric conversion elements 1111 in the nth row to the signal wiring 182, whereby the amounts of charge on the signal wiring 182 are changed. In times t9 to t10, the control signal SH2 becomes a high level, and the output signals of the variable amplifiers 1312 are sampled by the sample-and-hold circuits 1313$b$ as in times t5 to t6. The signals of the sample-and-hold circuits 1313$a$ and 1313$b$ are output to the signal processing unit 140 via the multiplexer 132 and the A/D converter 134. The signal processing unit 140 records differences between the respective signals from the sample-and-hold circuits 1313$a$ and 1313$b$ as the amounts of charge read from the photoelectric conversion elements 1111 in the nth row. In the reading period, the radiation imaging apparatus 100-1 sequentially repeats the foregoing operation from the first row, whereby a two-dimensional radiographic image based on a radiation irradiation amount distribution is generated.

Figure 4:
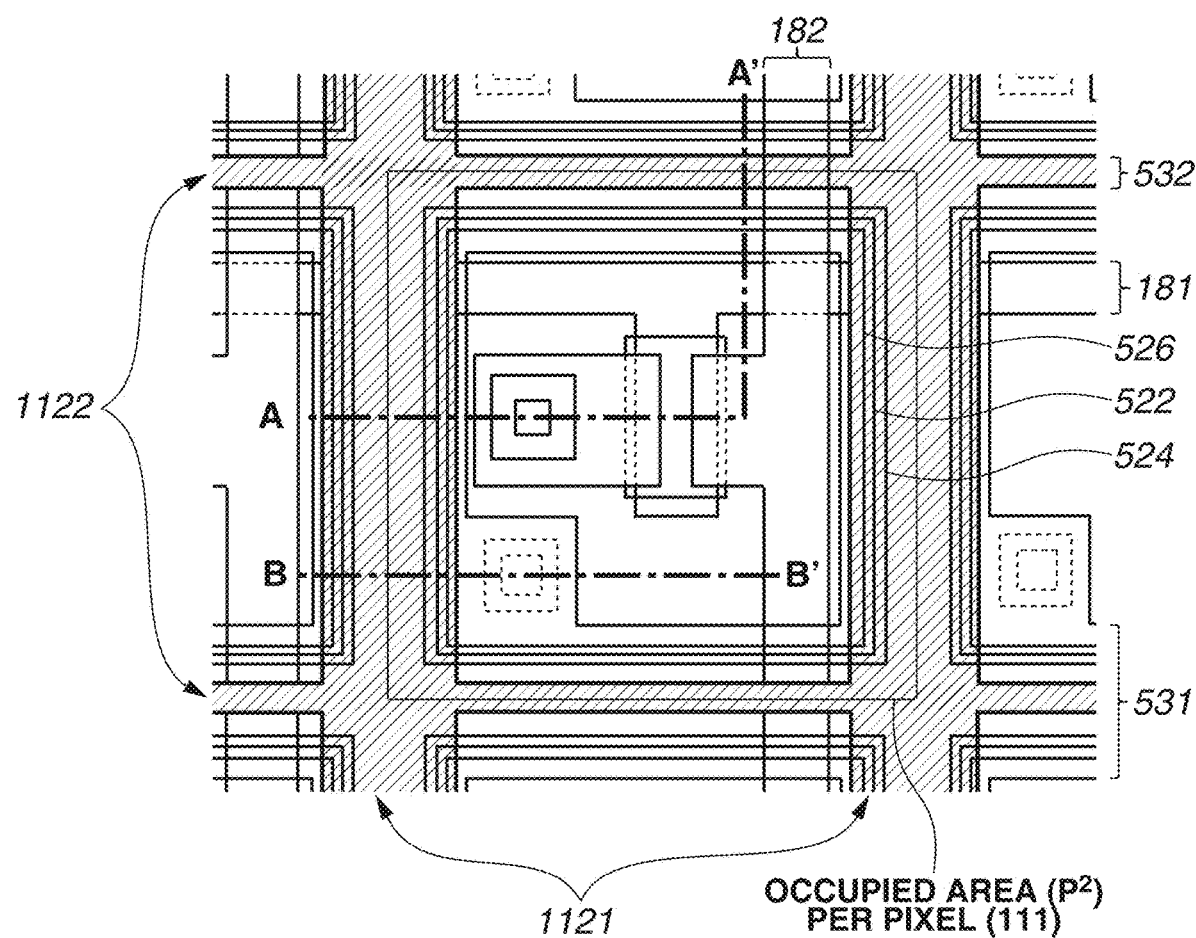
FIG. 4 is a diagram illustrating the first exemplary embodiment of the present disclosure, illustrating an example of a layout of pixels in the effective pixel region illustrated in FIGS. 2A and 2B.

FIG. 4 is a diagram illustrating the first exemplary embodiment of the present disclosure, illustrating an example of a layout of the pixels 111 in the effective pixel region 110$a$ illustrated in FIGS. 2A and 2B. In the present exemplary embodiment, a pixel pitch between adjoining pixels 111 will be denoted by P. Each pixel 111 is a square having a length of P on a side.

As illustrated in FIG. 4, the bias wiring 112 including the first wiring portions 1121 and the second wiring portions 1122 includes a metal layer 532 and a transparent conductive layer 531. The metal layer 532 is a non-transmissive member that reflects light occurring from the not-illustrated scintillator layer (specifically, scintillator layer 541 illustrated in FIGS. 5A and 5B) and does not transmit the light. The transparent conductive layer 531 is a transmissive member that transmits at least part of the light. Specifically, in the example illustrated in FIG. 4, the first wiring portions 1121 include the metal layer 532 that is a non-transmissive member, and the second wiring portions 1122 include the metal layer 532 that is a non-transmissive member and the transparent conductive layer 531 that is a transmissive member. The metal layer 532 is illustrated in gray in FIG. 4. In the example illustrated in FIG. 4, the metal layer 532 that is a non-transmissive member has a smaller line width in the second wiring portions 1122 than in the first wiring portions 1121 (in other words, a greater line width in the first wiring portions 1121 than in the second wiring portions 1122). For example, the metal layer 532 includes a metal layered structure of molybdenum and aluminum. The transparent conductive layer 531 is made of a transparent conductive oxide such as indium tin oxide (ITO).

The photoelectric conversion elements 1111 illustrated in FIGS. 2A and 2B each include a semiconductor layer 524 sandwiched between a first electrode 522 and a second electrode 526. If the semiconductor layer 524 is irradiated with the light occurring from the not-illustrated scintillator layer (specifically, scintillator layer 541 illustrated in FIGS. 5A and 5B), a charge is generated by photoelectric conversion in the semiconductor layer 524. When seen in a plan view, the greater the overlapping area of the metal layer 532 of the bias wiring 112 with the semiconductor layer 524, the lower the efficiency of light delivery to the semiconductor layer 524. In other words, the greater the overlapping area, the greater the loss of light due to the metal layer 532 that is a non-transmissive member. In the present exemplary embodiment, an opening ratio indicating the efficiency of light delivery is defined by the following Eq. (1):

$$\text{Opening ratio} = ((\text{area of the semiconductor layer 524}) - (\text{area of the overlap between the semiconductor layer 524 and the metal layer 532}))/P^2. \quad (1)$$

In Eq. (1), $P^2$ is an occupied area per pixel (111) as illustrated in FIG. 4. The pixels 111 according to the present exemplary embodiment have an opening ratio of 88%, for example. In the present exemplary embodiment, as described above, the line width of the metal layer 532 in the second wiring portions 1122 is smaller than that of the metal layer 532 in the first wiring portions 1121. The area of the overlap between the semiconductor layer 524 and the metal layer 532 in the second wiring portions 1122 is thus smaller than the area of the overlap between the semiconductor layer 524 and the metal layer 532 in the first wiring portions 1121. This makes the loss of light incident on the photoelectric conversion elements 1111 due to the second wiring portions 1122 of the bias wiring 112 smaller than that of light incident on the photoelectric conversion elements 1111 due to the first wiring portions 1121 of the bias wiring 112, whereby the opening ratio can be increased.

Figure 5A:
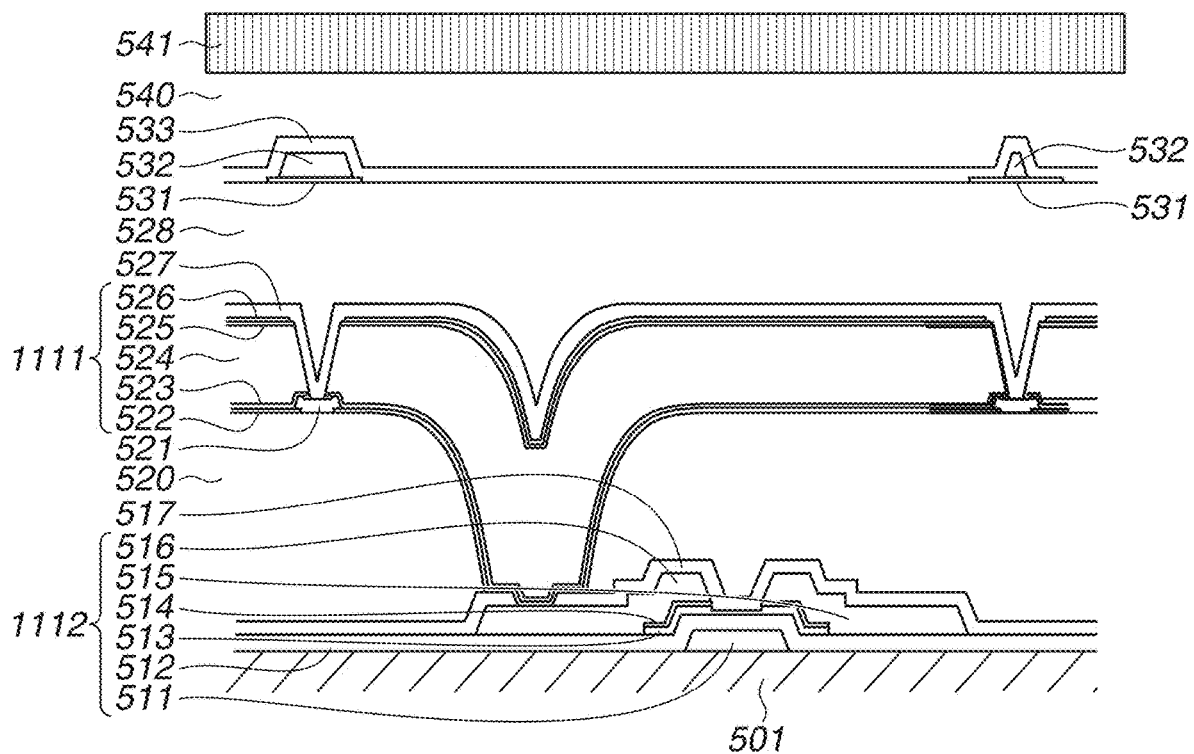
FIGS. 5A and 5B are diagrams illustrating examples of a layer structure in section A-A' and section B-B' illustrated in FIG. 4.
Figure 5B:
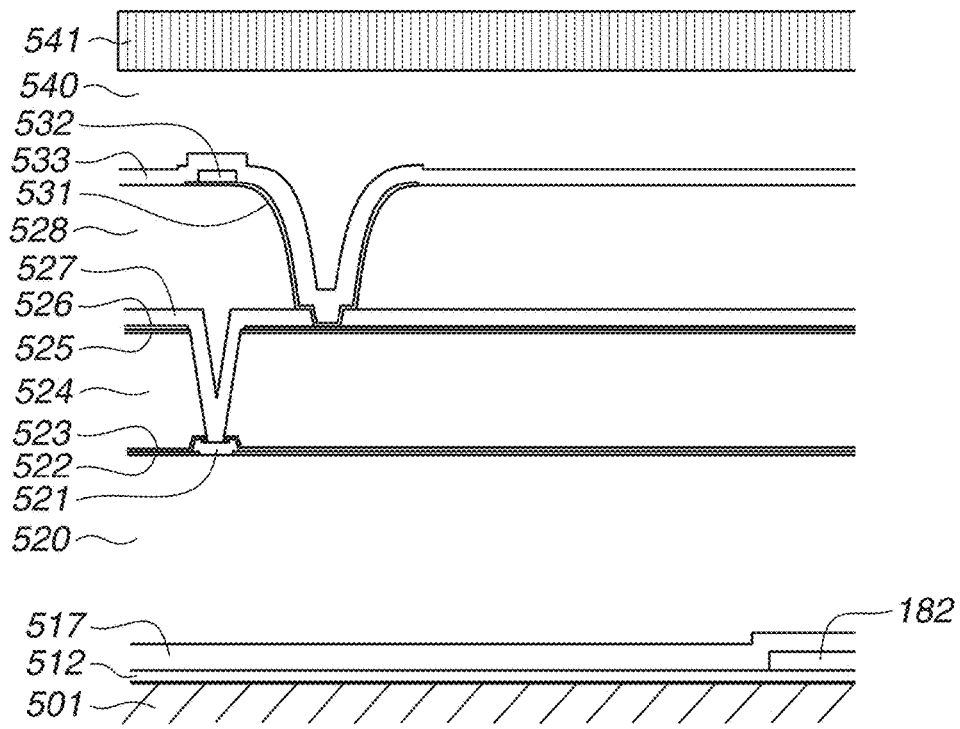

FIGS. 5A and 5B are diagrams illustrating examples of a layer structure in section A-A' and section B-B' illustrated in FIG. 4. Specifically, FIG. 5A illustrates an example of the layer structure in section A-A' illustrated in FIG. 4. FIG. 5B illustrates an example of the layer structure in section B-B' illustrated in FIG. 4.

The switch element 1112 includes a control electrode 511, an insulation layer 512, a semiconductor layer 513, an impurity semiconductor layer 514 having a impurity concentration higher than that of the semiconductor layer 513, a first main electrode 515, and a second main electrode 516 that are stacked on a substrate 501 in order from the substrate 501. The impurity semiconductor layer 514 is in contact with the first main electrode 515 and the second main electrode 516 at its respective partial areas. An area between the areas of the semiconductor layer 513 in contact with the partial areas constitutes a channel region of the switch element 1112. The control electrode 511 is electrically connected to the control wiring 181. The first main electrode 515 is electrically connected to the signal wiring 182. The second main electrode 516 is electrically connected to the first electrode 522 of the photoelectric conversion element 1111. In the present exemplary embodiment, the first main electrode 515 and the signal wiring 182 are integrally formed by using the same conductive layer, and the first main electrode 515 constitutes part of the signal wiring 182. A protective layer 517 covers the switch element 1112, the control wiring 181, and the signal wiring 182.

An interlayer insulation layer 520 is located between the substrate 501 and the plurality of first electrodes 522 of the photoelectric conversion elements 1111 so as to cover the plurality of switch elements 1112. The interlayer insulation layer 520 has contact holes. The first electrodes 522 of the photoelectric conversion elements 1111 and the second main electrodes 516 of the switch elements 1112 are electrically connected via the contact holes in the interlayer insulation layer 520.

The photoelectric conversion elements 1111 each include the first electrode 522, an impurity semiconductor layer 523 of first conductivity type, the semiconductor layer 524, an impurity semiconductor layer 525 of second conductivity type, and the second electrode 526 that are stacked on the interlayer insulation layer 520 in order from the interlayer insulation layer 520. In the present exemplary embodiment, the impurity semiconductor layer 523 is of n type, and the impurity semiconductor layer 525 p type. However, the conductivity types may be reversed. The metal layer 532 is electrically connected to the second electrode 526 of the photoelectric conversion element 1111 via the transparent conductive layer 531.

An insulation layer 527 and an interlayer insulation layer 528 cover the photoelectric conversion element 1111. The transparent conductive layer 531, the metal layer 532, a passivation layer 533, an interlayer insulation layer 540, and a scintillator layer 541 are stacked on the interlayer insulation layer 528 in order from the interlayer insulation layer 528.

For example, the scintillator layer 541 is a phosphor layer that converts radiations incident from above in FIGS. 5A and 5B into light. The present exemplary embodiment is configured so that part of the light occurring from the scintillator layer 541 is incident on the semiconductor layer 524 of the photoelectric conversion element 1111. As illustrated in FIGS. 5A and 5B, the transparent conductive layer 531 and the metal layer 532 constituting the bias wiring 112 are located on the incident side of the photoelectric conversion element 1111 in terms of the light from the scintillator layer 541.

Figure 6:
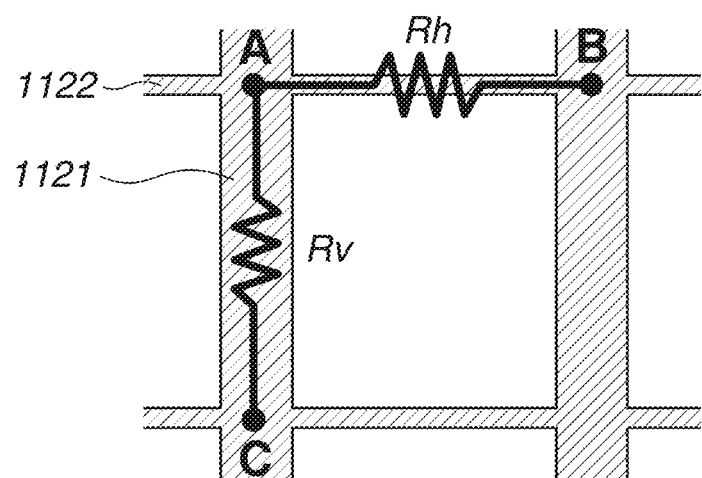
FIG. 6 is a diagram illustrating a concept of resistances of first and second wiring portions per pixel in the layout of the pixels illustrated in FIG. 4.

FIG. 6 is a diagram illustrating a concept of the resistance Rv of the first wiring portion 1121 and the resistance Rh of the second wiring portion 1122 per pixel 111 in the layout of the pixels 111 illustrated in FIG. 4. In FIG. 6, the resistance Rv of the first wiring portion 1121 per pixel 111 corresponds to the resistance between points A and C. The resistance Rh of the second wiring portion 1122 per pixel 111 corresponds to the resistance between points A and B. The resistances Rv and Rh each can be determined as a parallel connection of the electrical resistances of the metal layer 532 and the transparent conductive layer 531 between the respective points. Since the transparent conductive layer 531 made of ITO has electric conductivity lower than that of metals such as Al, the resistances Rv and Rh according to the present exemplary embodiment are substantially determined by the line width of the metal layer 532.

Figure 7A:
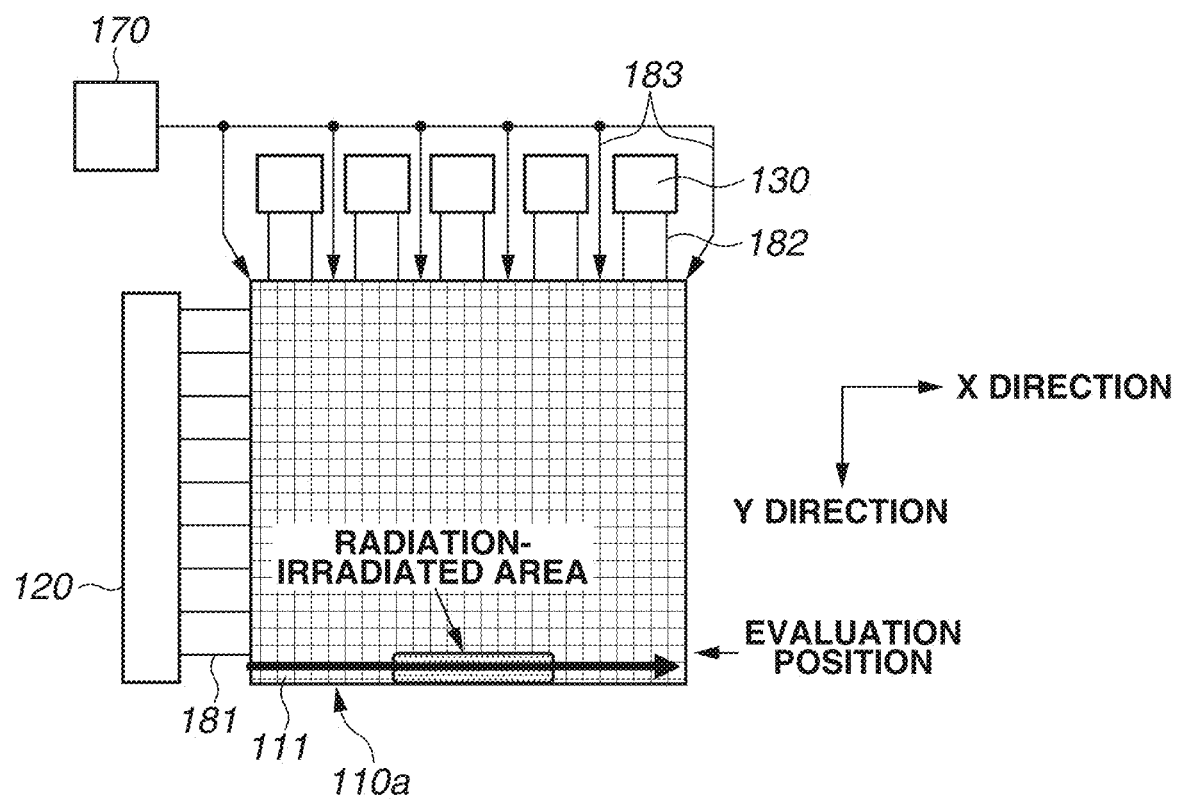
FIGS. 7A and 7B are diagrams illustrating the first exemplary embodiment of the present disclosure, illustrating an example of a method for evaluating crosstalk and a lateral distribution of crosstalk.
Figure 7B:
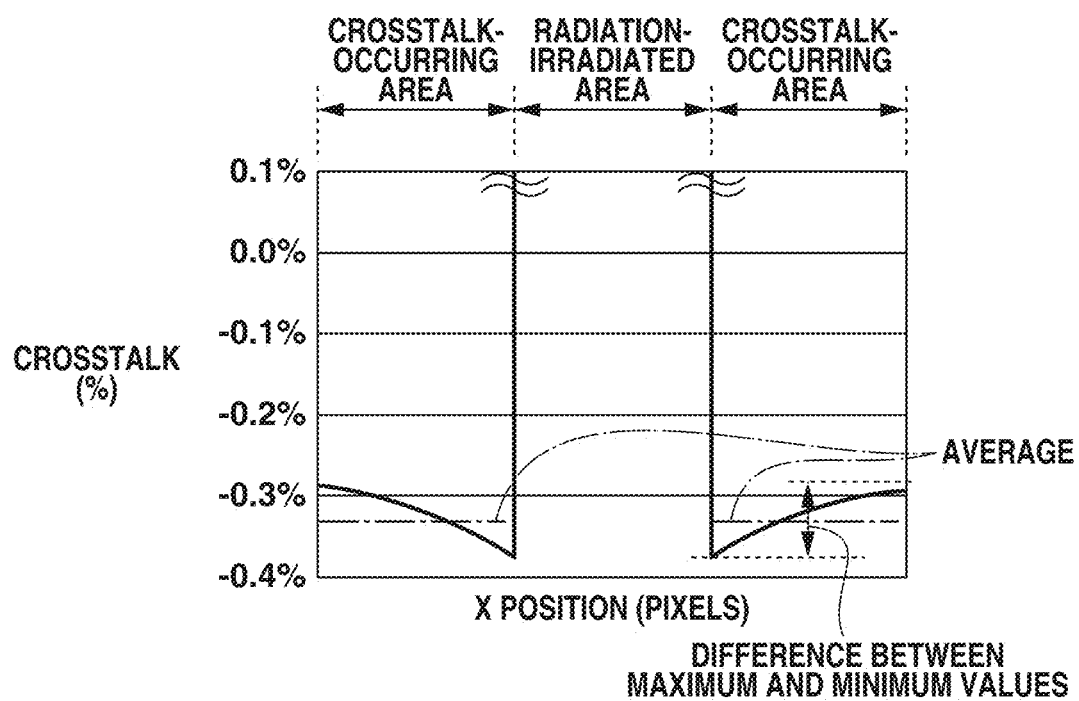

FIGS. 7A and 7B are diagrams illustrating the first exemplary embodiment of the present disclosure, illustrating an example of a method for evaluating crosstalk and a lateral distribution of crosstalk. Specifically, FIG. 7A illustrates an example of the method for evaluating crosstalk. FIG. 7B illustrates an example of the lateral distribution of crosstalk.

FIG. 7A will initially be described. In FIG. 7A, components similar to those illustrated in FIG. 1 are designated by the same reference numerals. A detailed description thereof will be omitted. In FIG. 7A, the effective pixel region 110a includes approximately 3000×3000 pixels 111. A plurality of chips of reading circuits 130 is connected to the top side (corresponding to the "second side 110a2" in FIG. 1) of the effective pixel region 110a. The bias voltage is supplied from the power supply circuit 170 via a plurality of bias supply lines 183 between and on both sides of the reading circuits 130. Approximately one-third area (with a width of approximately 1000 pixels) in the center of the bottommost row of the effective pixel region 110a (row farthest from the top side (corresponding to the "second side 110a2" in FIG. 1) where the power supply circuit 170 is electrically connected) is irradiated with radiations having a high intensity to generate a large amount of charge in the photoelectric conversion elements 1111 in this portion. The magnitude of crosstalk between the pixels 111 here is given by the following Eq. (2):

Crosstalk (%)=((amount of charge read from each pixel 111)/(amount of charge given to each photoelectric conversion element 1111 in the radiation-irradiated area))÷(⅓)    (2)

In Eq. (2), (⅓) at the end is a correction factor derived from the fact that the width of the radiation-irradiated region is ⅓ that of the effective pixel region 110a.

Next, FIG. 7B will be described. FIG. 7B illustrates an example of the lateral distribution of crosstalk obtained by the evaluation method illustrated in FIG. 7A. The pixels 111 other than in the radiation-irradiated area output non-zero charges to the reading circuits 130 even though the amounts of charge generated in the photoelectric conversion elements 1111 are zero. The output non-zero charges have a sign opposite to that of the charges read from the pixels 111 in the radiation-irradiated area. The crosstalk thus has a negative value. The present exemplary embodiment uses the following crosstalk evaluation indexes A and B:
A: Average crosstalk (%) in crosstalk-occurring areas (⅔ area not irradiated with the radiations), which corresponds to "average" in FIG. 7B; and
B: Crosstalk distribution ("difference between maximum and minimum values" in FIG. 7B).

Human eyes typically have sensitivity equivalent to 8 bits (¹⁄₂₅₆) with respect to a light and dark gray scale. To make crosstalk visually indiscernible, at least the absolute value (value without a negative sign) of the foregoing average crosstalk A may desirably be less than 0.39%.

FIG. 8 is a chart illustrating examples of the opening ratio, the resistances Rv and Rh, and crosstalk calculations in each of exemplary embodiments of the present disclosure and comparative examples. In FIG. 8, the first exemplary embodiment represents the case where the layout of the pixels 111 in the effective pixel region 110a illustrated in FIG. 4 is used.

Figure 9A:
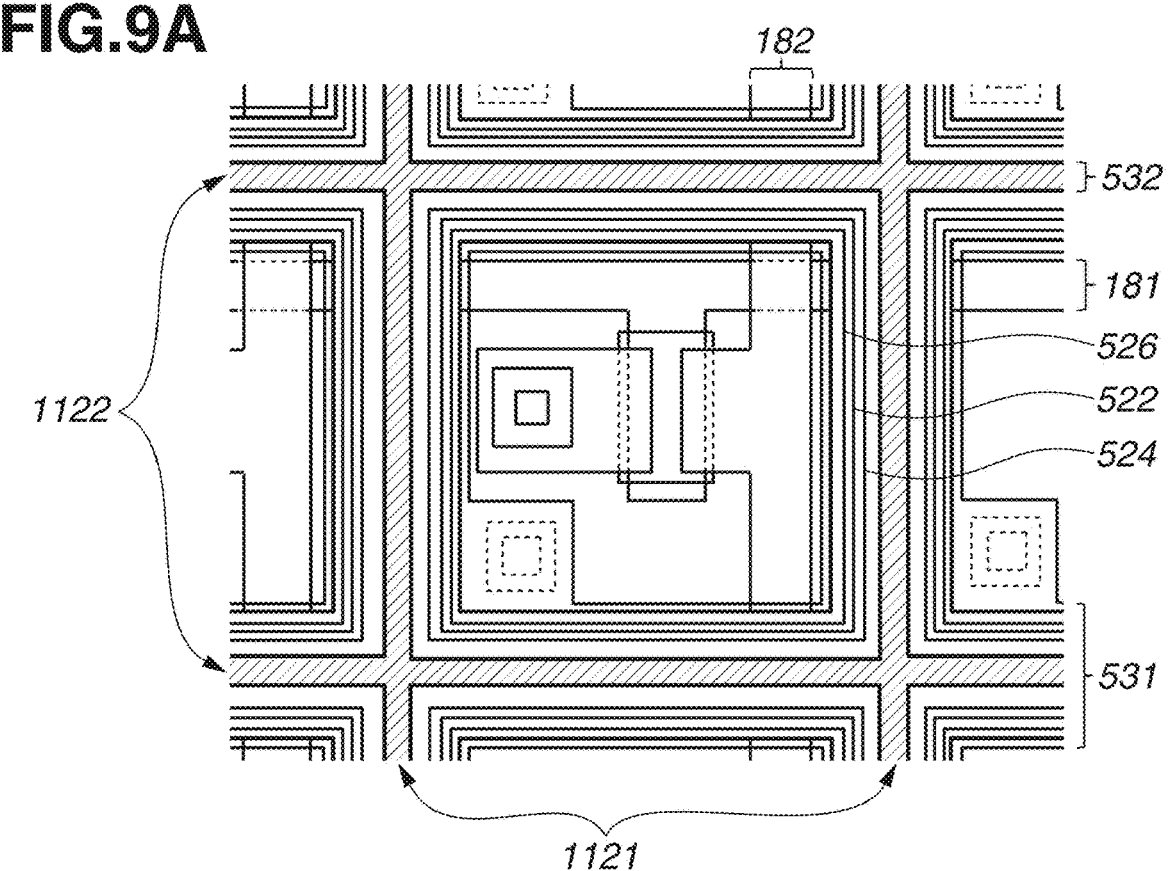
FIGS. 9A and 9B are diagrams illustrating examples of a layout of pixels in an effective pixel region according to first and second comparative examples illustrated in FIG. 8.
Figure 9B:
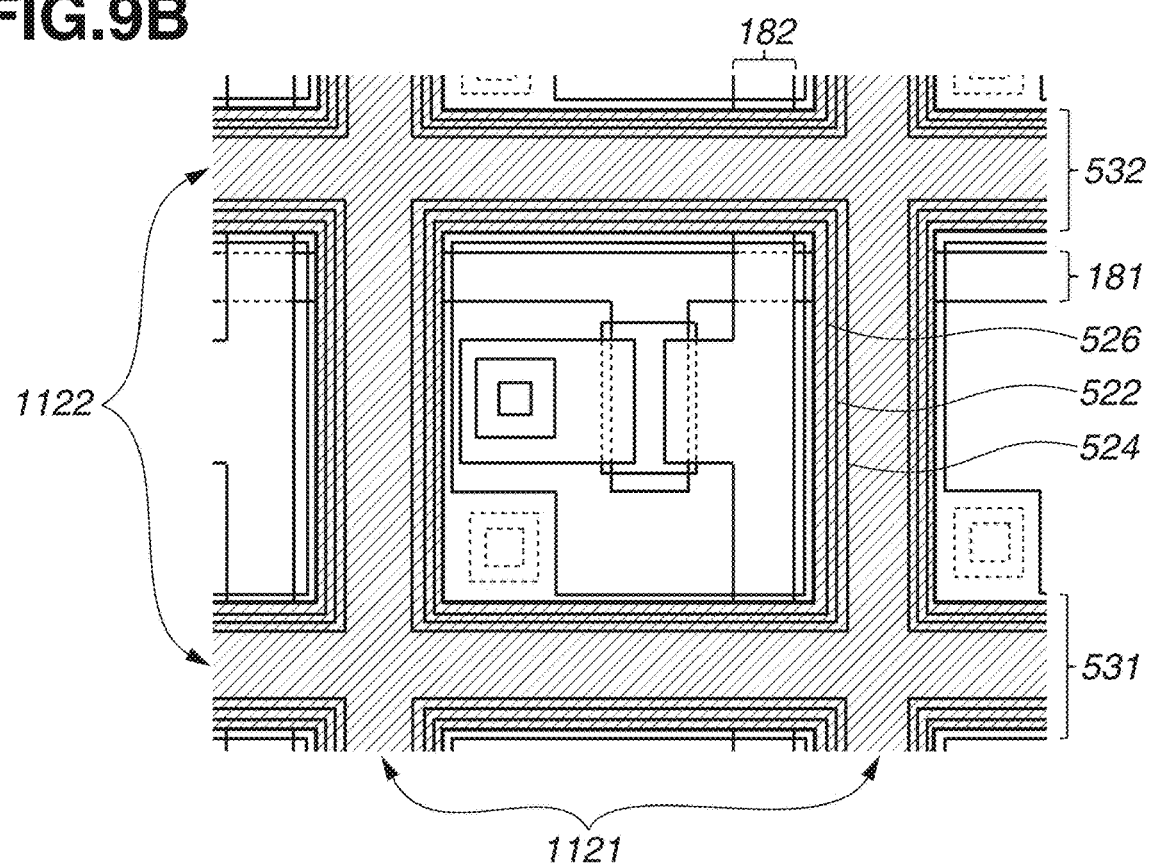

FIGS. 9A and 9B are diagrams illustrating examples of a layout of pixels 111 in an effective pixel region 110a according to a first comparative example and a second comparative example illustrated in FIG. 8. Specifically, FIG. 9A illustrates an example of the layout of the pixels 111 in the effective pixel region 110a according to the first comparative example illustrated in FIG. 8. FIG. 9B illustrates an example of the layout of the pixels 111 in the effective pixel region 110a according to the second comparative example illustrated in FIG. 8. FIGS. 9A and 9B will be described below in conjunction with a description of the first and second comparative examples, respectively.

In FIG. 8, the second exemplary embodiment represents a case where the layout of pixels 111 in an effective pixel region 110a illustrated in FIG. 13 to be described below is used. In FIG. 8, the crosstalk calculations include averages and distributions of crosstalk calculated by a Simulation Program for Integrated Circuit Emphasis (SPICE) simulation on the respective layouts of the pixels 111. In each case, the resistances Rv and Rh illustrated in FIG. 8 were set as a calculation condition.

In the first exemplary embodiment illustrated in FIG. 8, the resistance Rv was set to 1Ω and the resistance Rh was set to 5Ω as the calculation condition. In the first exemplary embodiment, an opening ratio of 88%, an average crosstalk of 0.16% in absolute value, and a crosstalk distribution of 0.01% were obtained. From the result of the first exemplary embodiment, it can be seen that a high opening ratio and low crosstalk can be achieved in a compatible manner.

First Comparative Example

Next, the layout of the pixels 111 in the effective pixel region 110a according to the first comparative example will be described with reference to FIG. 9A. In FIG. 9A, components similar to those illustrated in FIG. 4 are designated by the same reference numeral. A detailed description thereof will be omitted. In the first comparative example illustrated in FIG. 9A, the metal layer 532 in the first wiring portions 1121 has the same line width as the metal layer 532 in the second wiring portions 1122. The line widths are the same as the metal layer 532 in the second wiring portions 1122 illustrated in FIG. 4 (thin). The transparent conductive layer 531 is the same as described above. In the first comparative example illustrated in FIG. 8, the resistance Rv was set to 5Ω and the resistance Rh was set to 5Ω as the calculation condition. In the first comparative example, an opening ratio of 93%, an average crosstalk of 0.40% in absolute value, and a crosstalk distribution of 0.01% were obtained. According to the result of the first comparative example, the thin line width of the metal layer 532 both in the first and second wiring portions 1121 and 1122 contributes to the high operation ratio of 93% compared to the first exemplary embodiment. However, the absolute value of the average crosstalk increases beyond 0.39%. In short, low crosstalk is difficult to achieve in the first comparative example.

Second Comparative Example

Next, the layout of the pixels 111 in the effective pixel region 110a according to the second comparative example will be described with reference to FIG. 9B. In FIG. 9B, components similar to those illustrated in FIG. 4 are designated by the same reference numerals. A detailed description thereof will be omitted. In the second comparative example illustrated in FIG. 9B, the metal layer 532 in the first wiring portions 1121 has the same line width as the metal layer 532 in the second wiring portions 1122. The line widths are the same as the metal layer 532 in the first wiring portion 1121 illustrated in FIG. 4 (thick). The transparent conductive layer 531 is the same as described above. In the second comparative example illustrated in FIG. 8, the resistance Rv was set to 1Ω and the resistance Rh was set to 1Ω as the calculation condition. In the second comparative example, an opening ratio of 84%, an average crosstalk of 0.16% in absolute value, and a crosstalk distribution of 0.01% were obtained. According to the result of the second comparative example, the thick line width of the metal layer 532 both in the first and second wiring portions 1121 and 1122 contributes to the reduced absolute value of the average crosstalk as in the first exemplary embodiment. However, unlike the first exemplary embodiment, the opening ratio falls below 85%. In short, a high opening ratio is difficult to achieve in the second comparative example.

In the exemplary embodiments of the present disclosure, based on the results of FIG. 8, a range where the pixels 111 have an opening ratio of 85% or more and the absolute value of the average crosstalk occurring over the lateral direction (X direction, row direction, or second direction) is 0.39% or less is assumed. This can achieve a high opening ratio (85% or more) while reducing crosstalk to a degree visually indiscernible by human eyes (0.39% or less).

[Effective Range of Resistances Rv and Rh]

FIG. 10 is a chart illustrating examples of crosstalk calculations for various combinations of the resistances Rv and Rh illustrated as calculation conditions in FIG. 8. Specifically, FIG. 10 illustrates averages and distributions of crosstalk calculated of a layout of a N-row-by-M-column two-dimensional matrix of pixels 111 by a SPICE simulation with nos. #1 to #9, nine combinations of resistances Rv and Rh. In the calculation, N=M=3000. From FIG. 10, the following points (A) and (B) can be seen:

(A) The absolute value of the average crosstalk is determined by the resistance Rv and little affected by the resistance Rh.

(B) The magnitude of the crosstalk distribution is determined by the resistance Rh and not affected by the resistance Rv.

Figure 11A:
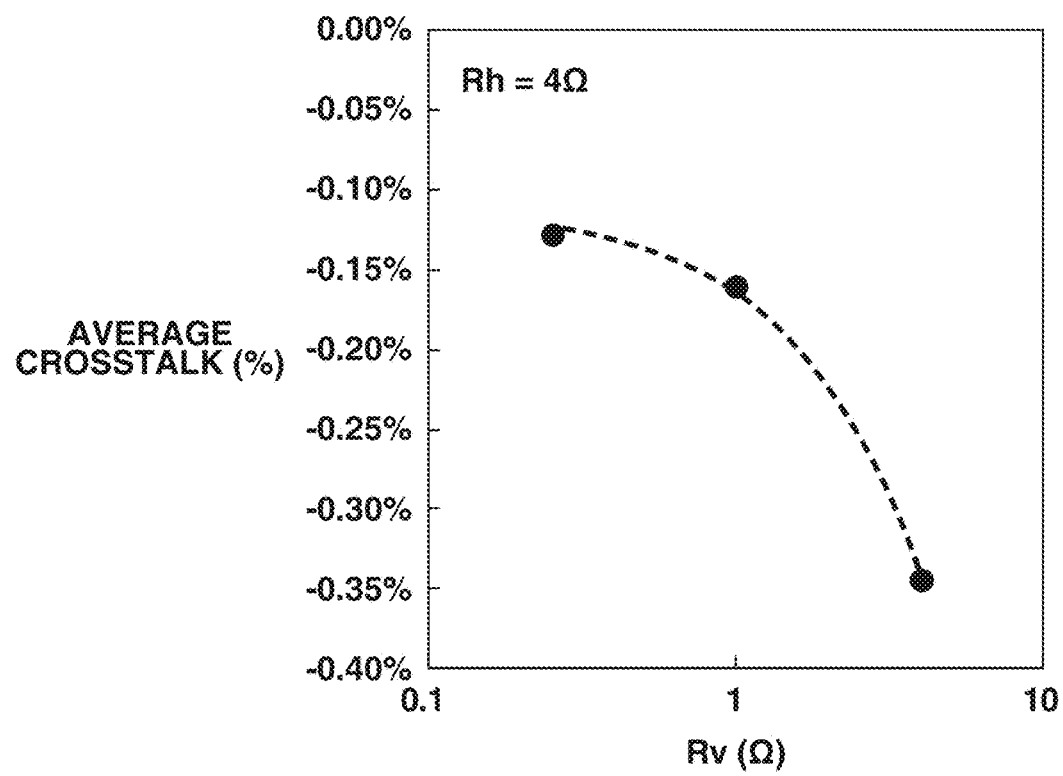
FIGS. 11A and 11B are charts for verifying dependence of average crosstalk and a crosstalk distribution on the resistances.
Figure 11B:
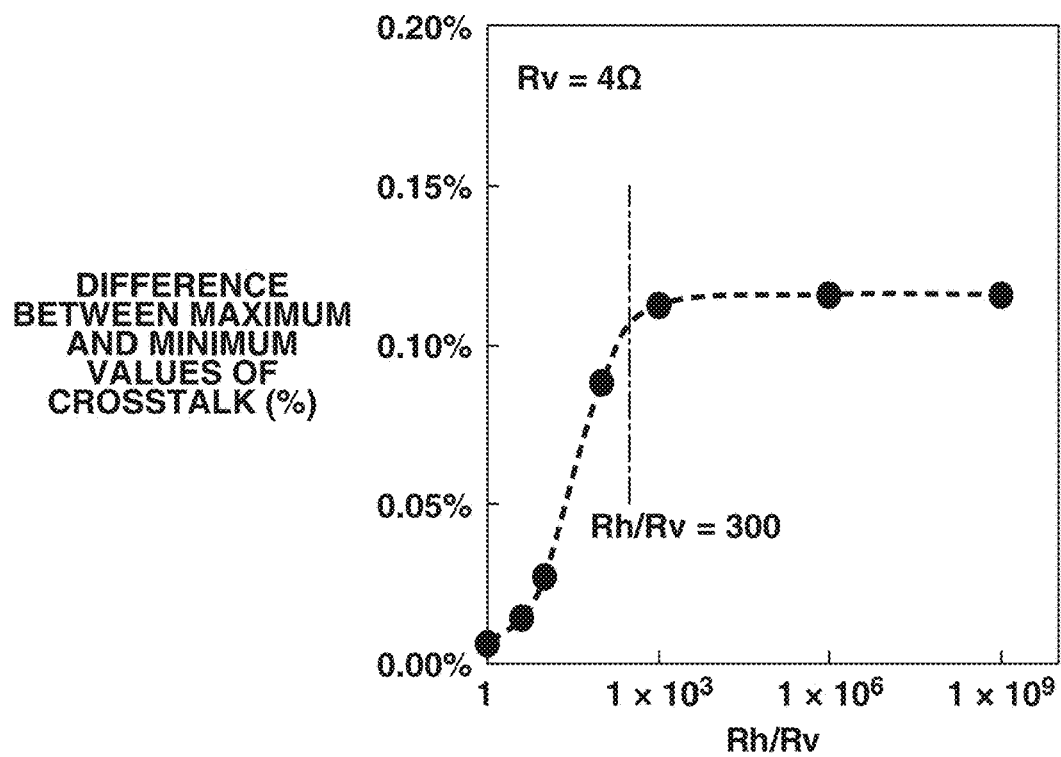

FIGS. 11A and 11B are charts for verifying the dependence of the average crosstalk and distribution on the resistances Rv and Rh. Specifically, FIG. 11A is a plot of the average values of crosstalk in nos. #1 to #3 of FIG. 10 with respect to the resistance Rv. If the resistance Rv is 4Ω or less, the absolute value of the average crosstalk is 0.39% or less. The smaller the resistance Rv, the closer to zero the absolute value of the average crosstalk.

FIG. 11B is a plot of the crosstalk distributions in nos. #3 to #9 of FIG. 10 with respect to the ratio Rh/Rv. The distribution has a constant value at Rh/Rv>300 or so. The distribution decreases at Rh/Rv≤300 or so.

Figure 12A:
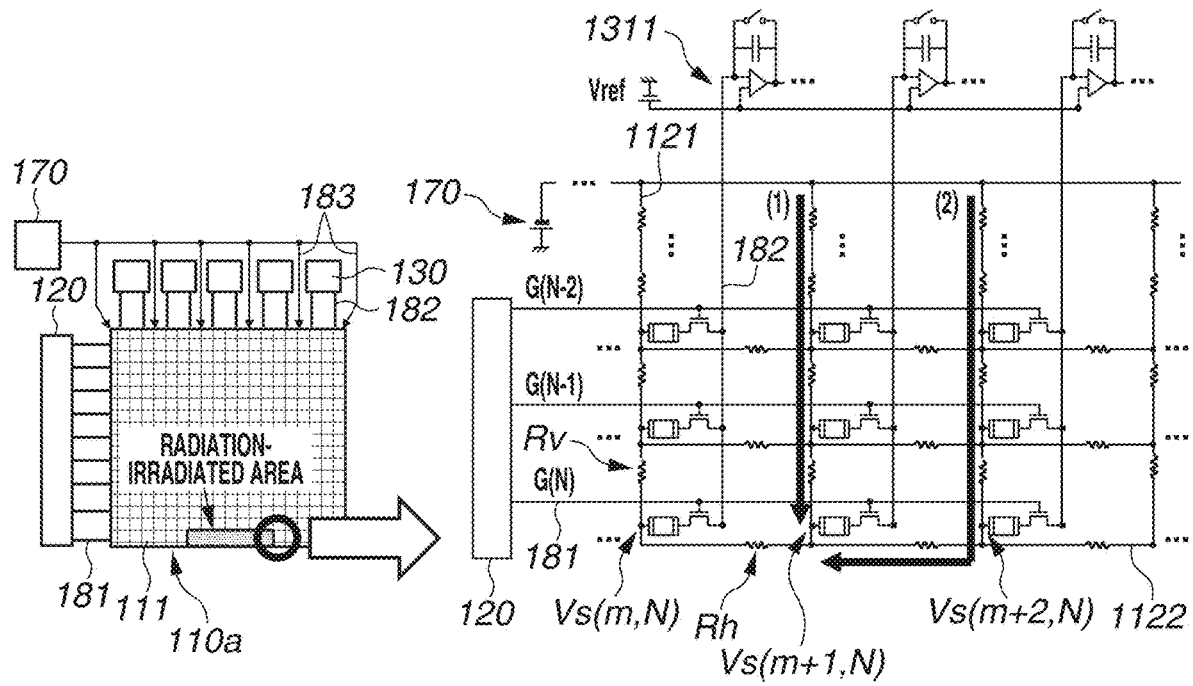
FIGS. 12A and 12B are diagrams for describing the principle of generation of crosstalk.
Figure 12B:
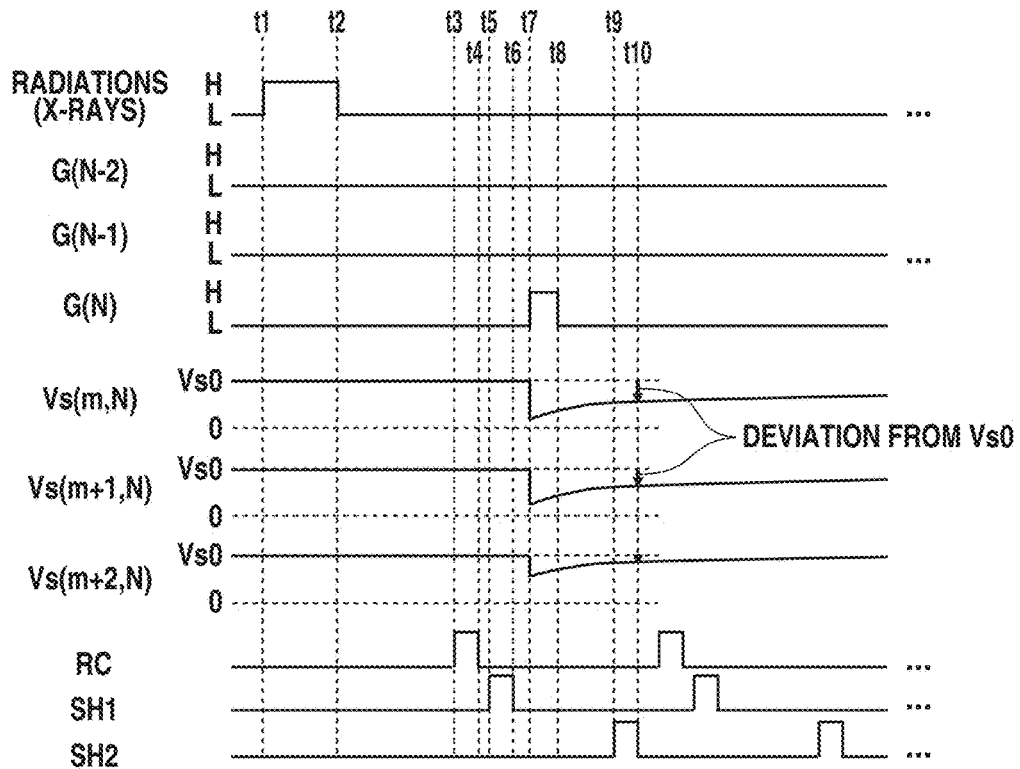

Possible reasons for the dependence verified by using FIGS. 11A and 11B will be described with reference to FIGS. 12A and 12B. FIGS. 12A and 12B are diagrams for describing the principle of generation of crosstalk. Specifically, FIG. 12A illustrates an example of an enlarged equivalent circuit diagram near the right end of the radiation-irradiated area (bottommost row of the N-row-by-M-column pixel matrix, i.e., the Nth row) illustrated in FIG. 7A. In FIG. 12A, components similar to those illustrated in FIGS. 2A and 2B are designated by the same reference numerals. A detailed description thereof will be omitted. FIG. 12B illustrates an example of a timing chart of the equivalent circuit illustrated in FIG. 12A.

In FIG. 12A, the radiation-irradiated area extends up to the mth column. Pixels 111 in the (m+1)th and subsequent columns are not irradiated with radiations but produce crosstalk. Bias voltages Vs applied to the photoelectric conversion elements 1111 of the radiation-irradiated pixel in the mth column and the non-radiation-irradiated pixels in the (m+1)th and (m+2)th columns will be denoted by Vs(m, N), Vs(m+1, N), and Vs(m+2, N), respectively. The bias voltages Vs(m, N), Vs(m+1, N), and Vs(m+2, N) have an initial value of Vs0 before radiation irradiation.

The a-Si photoelectric conversion elements 1111 typically have an initial value Vs0 of around several volts to 10 volts. The initial value Vs0 is a positive or negative value depending on the polarity of the photoelectric conversion elements 1111. For ease of description, in the present exemplary embodiment, the initial value Vs0 is described as a positive value. Between times t1 and t2 in FIG. 12B, the pixels 111 to be irradiated with radiations are irradiated with radiations, and charge occurs in the photoelectric conversion elements 1111. At time t7, the potential of the control line G(N) becomes a high level. The switch elements 1112 of the pixels 111 in the Nth row become conducting, and the bias voltage Vs(m, N) of the radiation-irradiated pixel (mth column) drops instantaneously. Meanwhile, the common electrodes of adjoining pixels are vertically and laterally connected via the bias wiring 112. Common electrode potentials of the non-radiation-irradiated pixels are thus affected as well, and the bias voltages Vs(m+1, N) and Vs(m+2, N) also drop instantaneously. The closer to the radiation-irradiated pixels, the greater the amounts of drop in the bias voltage.

Subsequently, currents flow into the common electrodes of these pixels 111 from the power supply circuit 170, and the bias voltages Vs(m, N), Vs(m+1, N), and Vs(m+2, N) recover gradually toward the initial value Vs0. While the bias voltages Vs are changing (have not recovered to the initial value Vs0 yet), the amounts of charge (not illustrated) on the respective lines of the signal wiring 182 and the outputs of the variable amplifiers 1312 are also deviated from the original values. Suppose that the sample-and-hold circuits 1313b of the reading circuit 130 operate at time t10 and settle the amounts of charge on the signal wiring 182 with the bias voltages Vs lagging behind in recovery and being still deviated from the initial value Vs0. In such a case, the amounts of deviation of the amounts of charge on the signal wiring 182 from the original values appear in the image. This results in crosstalk.

In the process of recovery of the foregoing bias voltages Vs, a current flows into the common electrode of a crosstalk-occurring pixel (for example, (m+1, N)) through a plurality of current flow-in paths, including:
(1) A "vertical path" via the first wiring portions 1121 of the N pixels in the same column ((m+1)th column); and
(2) A "vertical and lateral path" via the first wiring portions 1121 of the N pixels in an adjoining column ((m+2)th column) and the second wiring portion 1122 of a pixel.

The current flow-in paths also include "vertical and lateral paths" via the first wiring portions 1121 in the columns further on the right ((m+3)th and subsequent columns) and the second wiring portions 1122 of two or more pixels.

FIG. 12A illustrates the foregoing paths (1) and (2). If "vertical paths" (1) have a small resistance, all the bias voltages Vs including the bias voltages Vs(m, N), Vs(m+1, N), and Vs(m+2, N) recover more quickly on the whole and the average crosstalk decreases. The absolute value of the average crosstalk is thus determined by the resistance Rv as described in the foregoing point (A).

On the other hand, if "vertical and lateral paths" (2) have a small resistance, currents are simultaneously supplied through a plurality of vertical first wiring portions 1121. This laterally evens out local variations in the bias voltage Vs to reduce a difference (distribution) between the maximum and minimum values of crosstalk. The magnitude of the crosstalk distribution is thus determined by the resistance Rh as described in the foregoing point (B). The crosstalk distribution is sufficiently reduced if the currents are smoothly supplied to the crosstalk-occurring pixels by using both the "vertical path" and the "vertical and lateral paths". Specifically, with attention focused on the current flow-in path (2) as a representative of the "vertical and lateral paths", the lateral resistance per pixel (Rh) may desirably be sufficiently smaller (by one digit or so) than the vertical resistance of the N pixels (N×Rv). In other words, the following Exp. (3) may desirably be satisfied:

$$(Rh)/(N \times Rv) \leq 1/10. \quad (3)$$

If N is around 3000, the condition of Exp. (3) is satisfied by Rh/Rv≤300. This is considered to be the reason for the improvement of the distribution at Rh/Rv≤300 in FIG. 11B.

Consequently, in the exemplary embodiments of the present disclosure, the resistances Rv and Rh desirably satisfy 1<Rh/Rv≤300.

In the present exemplary embodiment, in view of reduction in the absolute value of the average crosstalk, the first wiring portions 1121 of the bias wiring 112 in the Y direction include the metal layer 532 having a sufficient line width to reduce the resistance Rv. To reduce the loss of light incident on the photoelectric conversion elements 1111 due to the metal layer 532 as much as possible, the metal layer 532 is disposed at pixel borders. Meanwhile, the average crosstalk does not deteriorate even if the second wiring portions 1122 of the bias wiring 112 have a resistance Rh greater than Rv.

The ratio of the resistances Rh/Rv can be set such that the crosstalk distribution has a desired value or less. In the present exemplary embodiment, 1<Rh/Rv. In view of a higher opening ratio, the second wiring portions 1122 of the bias wiring 112 in the X direction are formed so as to include the metal layer 532 of a smaller line width than the first wiring portions 1121 of the bias wiring 112.

As described above, according to the first exemplary embodiment, low crosstalk can be achieved with a high opening ratio.

Next, the second exemplary embodiment of the present disclosure will be described. In the following description of the second exemplary embodiment, a description of similarities to the foregoing first exemplary embodiment will be omitted, and differences from the foregoing first exemplary embodiment will be described.

A radiation imaging apparatus according to the second exemplary embodiment has a schematic configuration similar to that of the radiation imaging apparatus 100-1 according to the first exemplary embodiment illustrated in FIG. 1. The effective pixel region 110a and reading circuits 130 according to the second exemplary embodiment have an internal configuration similar to that of the effective pixel region 110a and the reading circuits 130 according to the first exemplary embodiment illustrated in FIGS. 2A and 2B.

Figure 13:
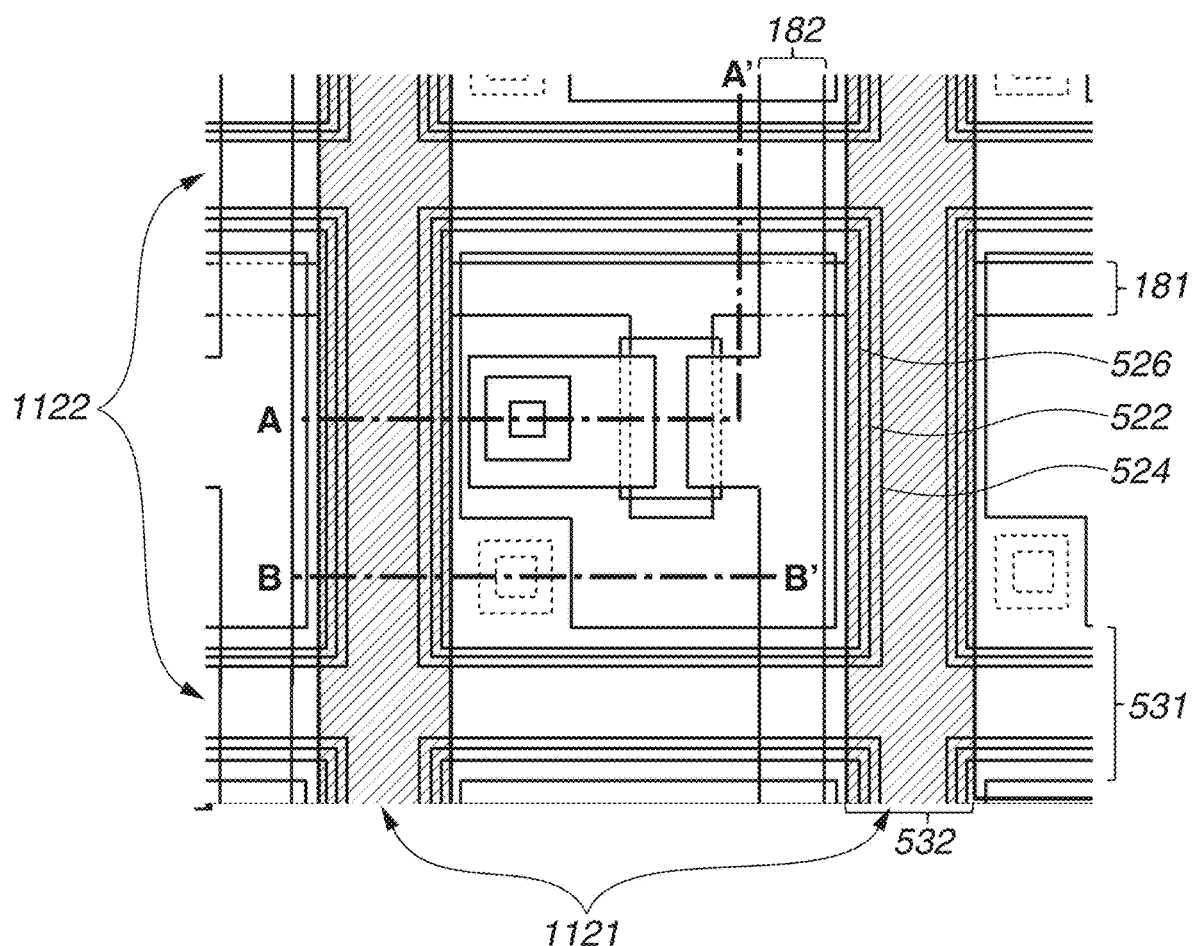
FIG. 13 is a diagram illustrating a second exemplary embodiment of the present disclosure, illustrating an example of the layout of pixels in the effective pixel region illustrated in FIGS. 2A and 2B.

FIG. 13 is a diagram illustrating the second exemplary embodiment of the present disclosure, illustrating an example of the layout of the pixels 111 in the effective pixel region 110a illustrated in FIGS. 2A and 2B. In FIG. 13, components similar to those illustrated in FIG. 4 are designated by the same reference numerals. A detailed description thereof will be omitted. Again, in the present exemplary embodiment, the pixel pitch between adjoining pixels 111 will be denoted by P. Each pixel 111 is a square having a length of P on a side.

Figure 14:
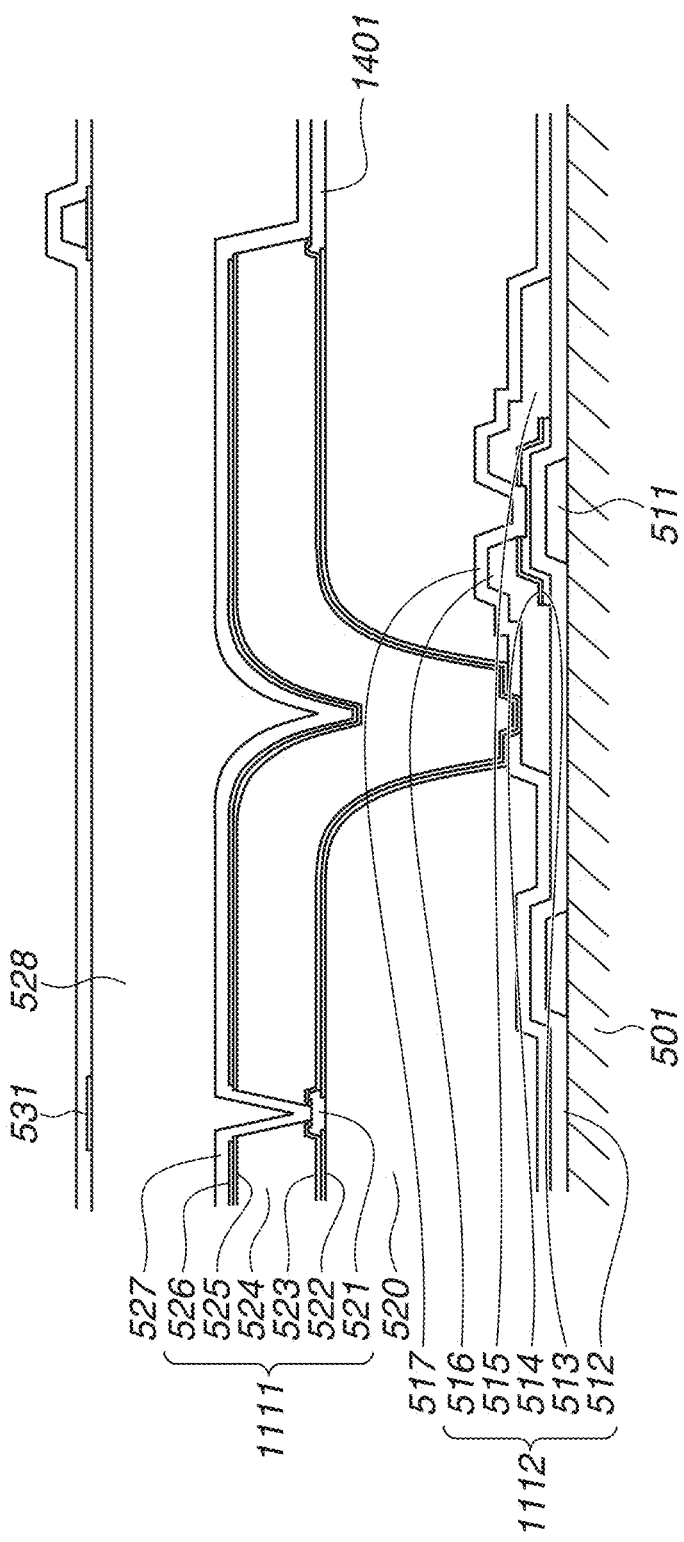
FIG. 14 is a diagram illustrating an example of a layer structure in section A-A' illustrated in FIG. 13.

FIG. 14 is a diagram illustrating an example of a layer structure in section A-A' illustrated in FIG. 13. In FIG. 14, components similar to those illustrated in FIGS. 5A and 5B are designated by the same reference numerals. A detailed description thereof will be omitted. In FIG. 14, the interlayer insulation layer 540 and the scintillator layer 541 illustrated in FIGS. 5A and 5B are omitted.

A difference between the layout of the pixels 111 in the effective pixel region 110a illustrated in FIG. 13 and the layout of the pixels 111 in the effective pixel region 110a according to the first exemplary embodiment illustrated in FIG. 4 is in the layer structure of the second wiring portions 1122 of the bias wiring 112. Specifically, in the second exemplary embodiment, the second wiring portions 1122 of the bias wiring 112 include the transparent conductive layer 531 that is a light transmissive member without the metal layer 532 that is a light non-transmissive member. Even in the second exemplary embodiment, the first wiring portions 1121 of the bias wiring 112 include the metal layer 532 as in the first exemplary embodiment.

In the second exemplary embodiment, since the second wiring portions 1122 of the bias wiring 112 include the transparent conductive layer 531 without the metal layer 532 that is a light non-transmissive member, the loss of light incident on the photoelectric conversion elements 1111 due to the second wiring portions 1122 can be made even smaller than in the first exemplary embodiment.

As illustrated in FIG. 8, the second exemplary embodiment provides an opening ratio of 90%, which is even higher than that in the first exemplary embodiment. Since the transparent conductive layer 531 has an electric conductivity lower than that of the metal layer 532, the resistances of the bias wiring 112 are Rv=300Ω and Rh=1Ω, i.e., the resistance Rv is higher than in the first exemplary embodiment. In the second exemplary embodiment, the crosstalk distribution is 0.07%, i.e., greater than in the first exemplary embodiment. However, the absolute value of the average crosstalk is reduced to 0.15%, which is on a level similar to that in the first exemplary embodiment.

According to the second exemplary embodiment, the opening ratio can be further increased in addition to the effect of the foregoing first exemplary embodiment.

Next, a third exemplary embodiment of the present disclosure will be described. In the following description of the third exemplary embodiment, a description of similarities to the foregoing first and second exemplary embodiments will be omitted, and differences from the foregoing first and second exemplary embodiments will be described.

Figure 15:
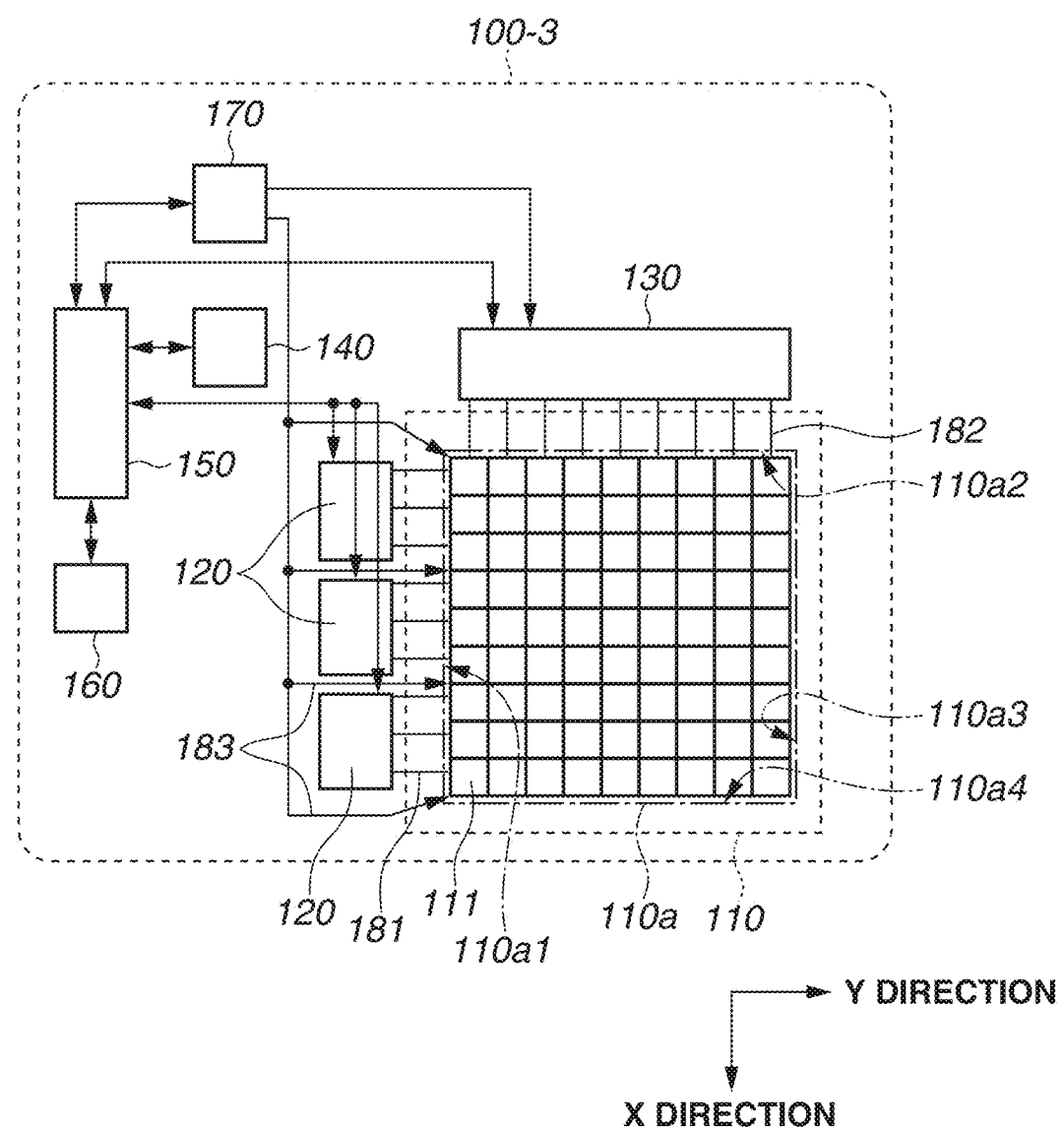
FIG. 15 is a diagram illustrating an example of a schematic configuration of a radiation imaging apparatus according to a third exemplary embodiment of the present disclosure.

FIG. 15 is a diagram illustrating an example of a schematic configuration of a radiation imaging apparatus 100 according to the third exemplary embodiment of the present disclosure. In the following description, the radiation imaging apparatus 100 illustrated in FIG. 15 will be referred to as a "radiation imaging apparatus 100-3". In FIG. 15, components similar to those illustrated in FIG. 1 are designated by the same reference numerals. A detailed description thereof will be omitted.

The radiation imaging apparatus 100-3 illustrated in FIG. 15 differs from the radiation imaging apparatus 100-1 illustrated in FIG. 1 in that the driving circuit 120 is configured as three separate chips, and that the power supply circuit 170 is electrically connected to the first side 110a1 of the effective pixel region 110a where the driving circuits 120 are electrically connected, via bias supply lines 183 located at four positions including between and on both sides of the three driving circuits 120.

As described above, in the radiation imaging apparatus 100-3 according to the third exemplary embodiment, the side of the effective pixel region 110a where the power supply circuit 170 is electrically connected is changed from that in the radiation imaging apparatus 100-1 according to the first exemplary embodiment. As illustrated in FIG. 15, the lateral direction will be defined as a Y direction (row direction or first direction), and the vertical direction an X direction (column direction or second direction). In the third exemplary embodiment, the wiring portions of the bias wiring 112 laid in the Y direction (row direction or first direction) serve as "first wiring portions 1121". The wiring portions laid in the X direction (column direction or second direction) serve as "second wiring portions 1122". The definitions of both the resistances Rv and Rh are therefore the same as in the first exemplary embodiment.

In the third exemplary embodiment, like the first exemplary embodiment, the first wiring portions 1121 of the bias wiring 112 in the Y direction are formed to include the metal layer 532 having a sufficient line width to reduce the resistance Rv for the sake of reduction in the absolute value of average crosstalk. In view of a high opening ratio, the second wiring portions 1122 of the bias wiring 112 in the X direction are formed to include the metal layer 532 having a line with smaller than in the first wiring portions 1121 of the bias wiring 112 or include the transparent conductive layer 531 without the metal layer 532.

According to the third exemplary embodiment, like the first exemplary embodiment, low crosstalk can be achieved with a high opening ratio.

Figure 16:
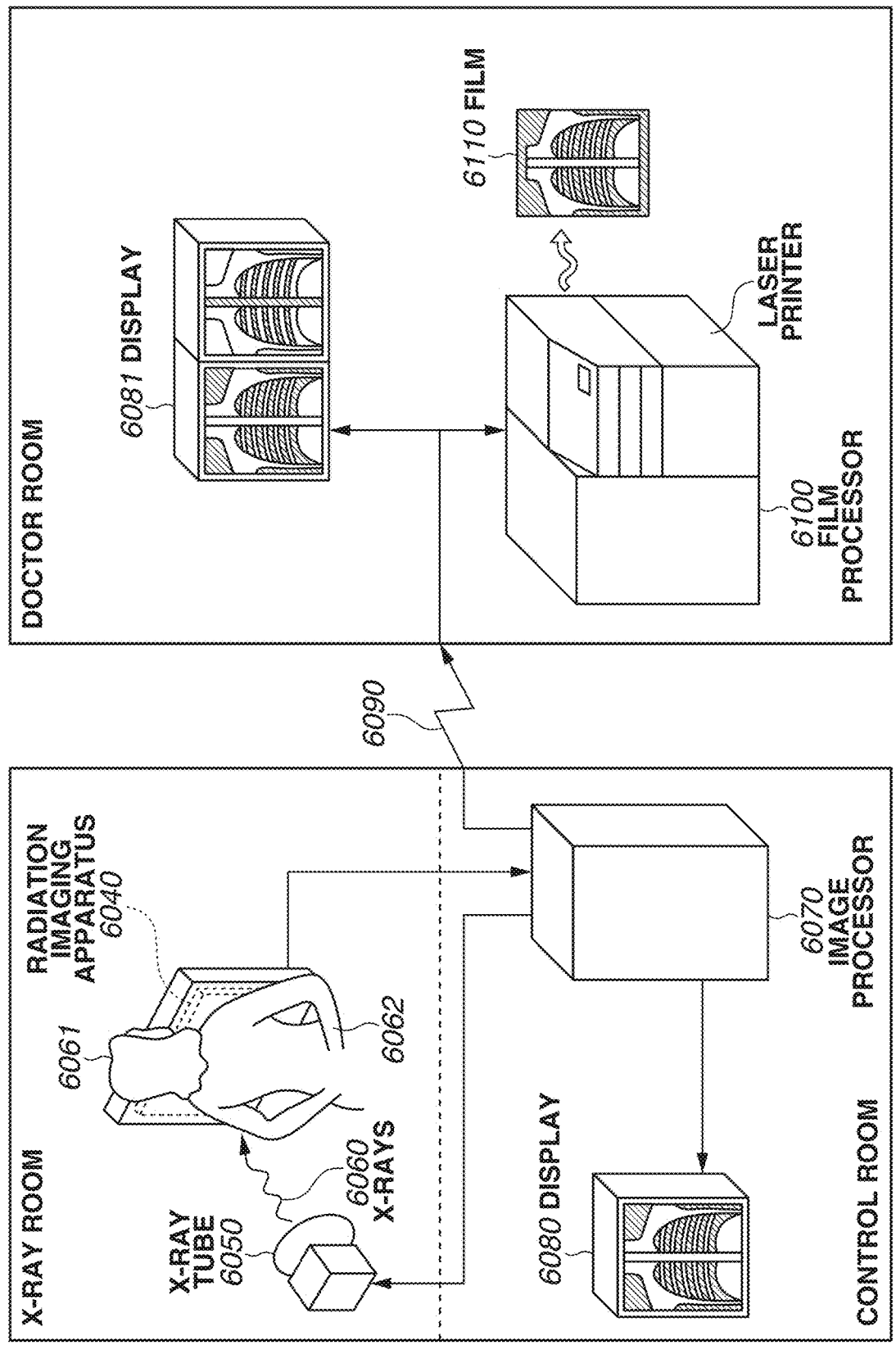

The radiation imaging apparatus 100 according to each of the exemplary embodiments is applicable to medical and nondestructive inspection applications. As an example, a radiation imaging system where any one of the foregoing radiation imaging apparatuses 100 is built in will be described below with reference to FIG. 16. An X-ray tube 6050 that is a radiation source for irradiating a radiation imaging apparatus 6040 (corresponding to any one of the foregoing radiation imaging apparatuses 100) with radiations generates X-rays 6060. The X-rays 6060 are transmitted through the chest 6062 of a patient or subject 6061 and incident on the radiation imaging apparatus 6040. The incident X-rays contain information inside the body of the patient or subject 6061. In the radiation imaging apparatus 6040, the scintillator layer emits light corresponding to the incidence of the X-rays 6060. The photoelectric conversion elements photoelectrically convert the light to obtain electrical information. The electrical information is digitally converted and subjected to image processing by an image processor 6070 serving as a signal processing unit. The resulting information can be observed on a display 6080 serving as a control room display.

The information can be transferred to a remote location by a transfer processing unit such as a network 6090. Examples of the network 6090 include a telephone line, a local area network (LAN), and the Internet. The information can thereby be displayed on a display 6081 that is a display unit in another place such as a doctor room, and a doctor can make a diagnosis at the remote location. The information can also be recorded on a recording medium such as an optical disk, and/or recorded on a film 6110 serving as a recording medium by a film processor 6100.

All the foregoing exemplary embodiments of the present disclosure are merely examples of embodiment in carrying out the present disclosure, and the technical scope of the present disclosure is not to be interpreted as limited thereto. Exemplary embodiments of the present disclosure can be implemented in various forms without departing from the technical concept or principal features of the present disclosure.

According to an exemplary embodiment of the present disclosure, low crosstalk can be achieved with a high opening ratio.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-243140, filed Dec. 26, 2018, which is hereby incorporated by reference herein in its entirety.

What is claimed is:

1. An imaging apparatus comprising:
a pixel region including a plurality of pixels arranged in a two-dimensional matrix, the pixels each including a photoelectric conversion element and a switch element electrically connected to one of electrodes of the photoelectric conversion element; and
bias wiring laid on a light incident side of the photoelectric conversion element to supply a bias from a power supply to each pixel in the pixel region from a side defining the pixel region, the bias wiring being laid around the pixel in a first direction away from the side and a second direction orthogonal to the first direction, the bias wiring being electrically connected to the other electrode of the photoelectric conversion element,
wherein the bias wiring includes a first wiring portion laid in the first direction and a second wiring portion laid in the second direction, and wherein a resistance of the first wiring portion per pixel is smaller than a resistance of the second wiring portion per pixel, and a loss of light incident on the photoelectric conversion element due to the second wiring portion is smaller than a loss of the light incident on the photoelectric conversion element due to the first wiring portion.

2. The imaging apparatus according to claim 1, wherein $1<Rh/Rv \leq 300$, where Rv is the resistance of the first wiring portion per pixel, and Rh is the resistance of the second wiring portion per pixel.

3. The imaging apparatus according to claim 1, wherein the first and second wiring portions of the bias wiring include a non-transmissive member configured not to transmit the light, and the non-transmissive member has a smaller line width in the second wiring portion than in the first wiring portion.

4. The imaging apparatus according to claim 1, wherein the first wiring portion of the bias wiring includes a non-transmissive member configured not to transmit the light, and the second wiring portion of the bias wiring includes a transmissive member configured to transmit the light.

5. The imaging apparatus according to claim 4,
wherein the non-transmissive member is a metal layer, and
wherein the transmissive member configured to transmit the light is a transparent conductive layer.

6. The imaging apparatus according to claim 1, further comprising:
a driving circuit configured to drive the pixels; and
a reading circuit configured to read an electrical signal from the pixels,
wherein the driving circuit and the reading circuit are each connected to a side defining the pixel region.

7. The imaging apparatus according to claim 1, further comprising a scintillator layer configured to convert an incident radiation into the light.

8. An imaging system comprising:
the imaging apparatus according to claim 1; and
a signal processing unit configured to process a signal from the imaging apparatus.

9. An imaging apparatus comprising:
a pixel region including a plurality of pixels arranged in a two-dimensional matrix, the pixels each including a photoelectric conversion element and a switch element electrically connected to one of electrodes of the photoelectric conversion element; and
bias wiring laid on a light incident side of the photoelectric conversion element to supply a bias from a power supply to each pixel in the pixel region from a side defining the pixel region, the bias wiring being laid around the pixel in a first direction away from the side and a second direction orthogonal to the first direction, the bias wiring being electrically connected to the other electrode of the photoelectric conversion element,
wherein the bias wiring includes a first wiring portion laid in the first direction and a second wiring portion laid in the second direction, and
wherein an opening ratio of the pixels based on the first and second wiring portions is 85% or more, and an absolute value of average crosstalk over the second direction is 0.39% or less.

10. An imaging system comprising:
the imaging apparatus according to claim 9; and
a signal processing unit configured to process a signal from the imaging apparatus.

* * * * *